といった | United States Patent [19]

Hawthorne

[11] Patent Number: 4,824,659
[45] Date of Patent: Apr. 25, 1989

[54] ANTIBODY CONJUGATES

[75] Inventor: Marion F. Hawthorne, Encino, Calif.

[73] Assignee: Immunomedics, Inc., Warren, N.J.

[21] Appl. No.: 742,436

[22] Filed: Jun. 7, 1985

[51] Int. Cl.$^4$ .......... A61N 5/12; A61K 49/02; A61K 31/74; A61K 42/02
[52] U.S. Cl. .......... 424/1.1; 424/9; 424/78; 424/85.8; 128/1.1; 530/387; 525/54.1; 600/4
[58] Field of Search .......... 424/1.1, 9, 78, 85; 128/1.1

[56] References Cited

U.S. PATENT DOCUMENTS

| | | | |
|---|---|---|---|
| 4,331,647 | 5/1982 | Goldenberg | 424/1.1 |
| 4,348,376 | 9/1982 | Goldenberg | 424/1.1 |
| 4,361,544 | 11/1982 | Goldenberg | 424/1.1 |
| 4,434,150 | 2/1984 | Azad et al. | 424/1.1 |
| 4,460,559 | 7/1984 | Goldenberg | 424/1.1 |
| 4,460,561 | 7/1984 | Goldenberg | 424/1.1 |
| 4,466,952 | 8/1984 | Hadd | 424/1.1 |
| 4,665,897 | 5/1987 | Lemelson | 128/1.1 |
| 4,674,480 | 6/1987 | Lemelson | 128/1.1 |

Primary Examiner—John F. Terapane
Assistant Examiner—J. E. Thomas
Attorney, Agent, or Firm—Bernhard D. Saxe

[57] ABSTRACT

An antibody or antibody fragment is modified by chemical linkage to a synthetic poly(amide/urea/thiourea) which contains a plurality of boron atoms or other functional groups, conferring upon the resultant conjugate desirable properties as a diagnostic and/or therapeutic agent. In a preferred embodiment, boron-containing groups are conjugated to the antibody/fragment such that the resultant conjugate contains 50–2000 boron atoms, with about 96% Boron-10 isotope content, to produce conjugates useful for neutron-activated radiotherapy of tumors or pathological lesions.

17 Claims, No Drawings

ANTIBODY CONJUGATES

BACKGROUND OF THE INVENTION

The present invention relates to an antibody or antibody fragment modified by chemical linkage to a synthetic poly(amide/urea/thiourea) which contains a plurality of boron atoms or other functional groups, conferring upon the resultant conjugate desirable properties as a diagnostic and/or therapeutic agent.

It is known to modify antibodies by chemically linking to them various types of addends. For example, enzymes have been linked to antibodies to make conjugates useful in ELISA immunoassays, boron-containing addends have been linked to antibodies and antibody fragments to produce therapeutic agents, and antibodies have been conjugated to polypeptides such as polylysine. European patent application No. 88,695, to McKearn et al., published 9/14/83, discloses antibodies conjugated to polypeptides made from natural amino acids, which in turn can carry a functional group such as a chelator, drug, toxin and the like.

It would be highly desirable to be able to modify an immunoglobulin to incorporate moieties that contain useful functionality, but in such a way that the addend is precisely defined in terms of its structure. This is particularly useful where it is desired to incorporate a plurality, especially a large number, of added functional groups such as chelating agents, boron-containing groups, radionuclides, spin labels and the like. In the past, it has been troublesome to attempt to characterize such modified antibodies because of the heterogeneity of the conjugates, and this has resulted in difficulties in assuring reproducibility of results. Moreover, it has been difficult to attach sufficient boron atoms to an antibody so that even a low percentage of conjugates localized in tumor or lesion tissue carries a large enough number of boron atoms to be therapeutically significant for neutron activated radiotherapy.

A need therefore continues to exist for chemically modified antibody conjugates having well-defined structures for the modifying groups to minimize the uncertainties in preparing and using these molecular species.

OBJECTS OF THE INVENTION

One object of the present invention is to provide an antibody conjugate having a sufficiently large number of boron atoms so that it will function as an efficient therapeutic agent for thermal neutron activated radiotherapy of tumors and pathological lesions.

Another object of the present invention is to provide a modified antibody or antibody fragment having a defined, chemically linked addend incorporating useful functional groups for diagnosis and/or therapy.

A further object of the invention is to provide reagents for use in modifying antibodies to confer upon the resultant conjugates desirable properties for diagnosis and/or therapy.

Yet another object of the invention is to provide agents useful for diagnosis and/or treatment of cancer, infectious lesions or other pathological lesions such as myocardial infarctions.

Other objects of the invention will become more readily apparent to those of ordinary skill in the art in light of the following discussion.

SUMMARY OF THE INVENTION

The foregoing objects can be achieved by providing a modified antibody or antibody fragment, consisting essentially of:

(1) at least one hypervariable region which specifically binds a ligand such that the formation of the resultant immunological complex is of diagnostic or therapeutic utility; and (2) at least one defined, substantially homogeneous synthetic poly(amide/urea/thiourea) which incorporates residues containing at least one of: (i) a plurality of Boron-10 atoms; (ii) a metal-chelating moiety; (iii) an antineoplastic agent; (iv) a paramagnetic spin label; (v) a radionuclide; (vi) a chemotherapeutic agent; (vii) a photosensitizer; (viii) a magnetic resonance imaging enhancer; (ix) an enzyme; (x) a chromogen; or (xi) a fluorescent marker;

wherein said synthetic poly(amide/urea/thiourea) is chemically bound to said antibody or antibody fragment at one or more sites which do not substantially interfere with the immunolocial specificity of said hypervariable region; and wherein a plurality of the residues making up said poly(amide/urea/thiourea) are not natural L-amino acids or are natural L-amino acids with modified side chains.

The present invention further provides antibody conjugates carrying functionality other than boron, reagents and methods for prepariang the foregoing antibody conjugates, as well as kits containing the conjugates and methods of using the conjugates for diagnosis and therapy.

DETAILED DESCRIPTION

The modified antibodies and antibody fragments according to the invention contain the hypervariable region, i.e., the region of the immunoglobulin which specifically binds the ligand which defines the specificity of the antibody, and at least one synthetic poly(amide/urea/thiourea) portion having a defined chemical structure, the poly(amide/urea/thiourea) being covalently linked to the immunoglobulin. Each poly(amide/urea/thiourea) portion of the molecule in turn is composed of residues containing the desired useful functionality and/or groups which improve the solubility properties, the separability properties, the comformational properties, or other properties of the resultant conjugate.

Schematically, the modified antibody of the invention can be represented as:

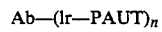

where Ab is an antibody or antibody fragment comprising at least one hypervariable region which specifically binds a ligand of interest, e.g., a marker produced by or associated with a tumor or a pathological lesion; lr is a linker function, which can simply be, e.g., an ester, amide, urea, carbamate, thiourea, ether or thioether bond, or a multifunctional linker which joins the poly(amide/urea/thiourea) addend to the antibody; "PAUT" is a poly(amide/urea/thiourea) having a defined chemical formula and incorporating the desired functionality; and n is an integer from 1 to 20, preferably from 1 to 10, and more preferably from 1 to 5. It will be appreciated that the addend denoted "lr—PAUT" may in fact be composed of several polymer chains joined to a multivalent linker, i.e., lr—(PAUT)$_m$, and that within the PAUT there may be one or more branch points.

As used in the context of this disclosure, the term "poly(amide/urea/thiourea)" (hereinafter "PAUT") denotes a sequenced polymer composed of residues, some or all of which contain a plurality of boron atoms or other useful diagnostic or therapeutic groups, the residues being linked by amide, urea and/or thiourea functions. Any single residue in the body of the polymer chain will normally be joined at two points to two adjacent residues, although it will be seen that additional points of attachment for a residue can be envisioned, e.g., for branching. Terminal residues will normally contain a functional group for linking the PAUT to the antibody. This can be a simple function, e.g., an isocyanate or isothiocyanate, a function capable of activation to bind to antibody, e.g., a carboxyl which can be activated by conversion to its anhydride, acid chloride, N-hydroxysuccinimide ester, or a more complex linking function such as one of those disclosed in greater detail hereinafter. Terminal residues not used for linkage to the antibody can be capped or used to bind other useful functions, e.g., chelators, drugs, toxins and the like, or they can be left unmodified.

In a preferred embodiment of the invention, the antibody conjugate would contain a large number of boron atoms, more preferably prepared from reagents enriched in Boron-10 isotope, boron-containing reagents enriched to about 96% Boron-10 being commercially available. Such a conjugate would be of great utility in neutron activated radiotherapy, since it could bring to a tumor site or the site of a pathological lesion a sufficient number of boron atoms to provide a therapeutic dosage of alpha particles to the surrounding tissue upon thermal neutron irradiation, even where the percentage of an injected dose of antibody conjugate which localizes in the target tissue is relatively low, e.g., 1–10%. Such localization percentages are not uncommon for antibody-based diagnostic and therapeutic agents.

Targeted neutron-activated radiotherapy is described, e.g., in Goldenberg et al., *Proc. Natl. Acad Sci. USA*, 81, 560 (1984); Hawthorne et al., *J. Med. Chem.*, 15, 449 (1972); and in Goldenberg, U.S. Pat. Nos. 4,331,647, 4,348,376, 4,361,544, 4,468,457, 4,444,744, 4,460,459 and 4,460,561, and in related pending applications U.S. Ser. Nos. 609,607 (filed 5-14-84) and 633,999 (filed 7-24-84), the disclosures of all of which are incorporated herein in their entireties by reference.

The aformentioned references disclose, inter alia, methods of incorporating Boron-10-containing addends into antibody conjugates using, e.g., coupling of a carborane (linked to a phenyldiazonium ion) to an antibody, which are suitable for incorporation of an relatively low number of Boron-10 atoms. Typically, between 10 and 120 B-10 atoms have been attached to IgG before the immunoreactivity and yield of recovered product become unacceptably low, using the carboranephenyldiazonium conjugation procedure. However, it would be preferable to be able to conjugate a larger number of B-10 atoms to an antibody so that even a low percentage of tumor accretion of an injected circulating antibody conjugate, e.g., on the order of 1.5%, would nonetheless carry hundreds of B-10 atoms per conjugate to the tumor site.

Several approaches to improving the efficiency of B-10 conjugation have been developed, most of which have related to improving the water solubility of the carborane addend by, e.g., using carborane monoanions or attaching polyhydroxylic tails to the carborane. See, e.g., Sneath et al., *J. Med. Chem.*, 17, 796 (1974); Sneath et al., *J. Med. Chem.*, 19, 1920 (1976); Hawthorne et al., *J. Am. Chem. Soc.*, 90, 862 (1968); and Mizusawa et al., *Proc. First Internatl. Symp. Neutron Capture Therapy*, Cambridge, MA., Oct. 12–14, 1983, pp 215–224. Other variants involve use of other functional groups instead of diazonium ions to effect conjugation to the antibody. The present method and reagents go well beyond these earlier approaches.

The boron-loaded antibody conjugates according to the present invention have a number of boron atoms per antibody molecule normally ranging from at least about 50 up to about 10,000, preferably from about 200 to about 2,000. To reiterate, these are preferably about 96% Boron-10 enriched, although it may be more cost-effective to use a conjugate having a larger number of boron atoms with the 20% natural abundance of Boron-10 isotope.

The boron-containing PAUT is conjugated to an antibody, which may be any type of immunoglobulin molecule having at least one hypervariable region, i.e., a region which specifially binds to an antigen of diagnostic and/or therapeutic interest. These include whole immunoglobulin, e.g., IgM, IgG, IgA, IgD, IgE and the like, or an immunoglobulin fragment, e.g., F(ab')$_2$, F(ab)$_1$, Fab, Fab' and the like, or a hybrid antibody or fragment. In this discussion, the term "antibody" will be used to signify any of the foregoing, unless otherwise specified.

The principal types of building blocks for the PAUT according to the invention are selected from amino acids, diamines, diacids, diisocyanates and diisothiocyanates containing boron functions therein, principally boron cage functions which have the advantage of high boron content and attractive chemical properties. The individual residues making up the synthetic PAUT are linked by amide(peptide) bonds, urea or thiourea functions. The amide bonds can be formed either by successive coupling of amino acids, e.g., alpha-amino acids or amino acids wherein the amine and carboxyl groups are farther removed from one another, or successive coupling of diamino groups to dicarboxylic acid groups in a "nylon 66" manner, i.e., with alternating senses of the amide bonds, viz., —NHCO—CONH—NH-CO—CONH—, or a mixture of such couplings. The urea and thiourea functions can be formed by condensation of a chain terminating in an amine function with an isocyanate or isothiocyanate, normally a diisocyanate or diisothiocyanate, used in excess to minimize cross-linking, and the reverse linkage of chains terminating with isocyanate/isothiocyanate functions to amine building blocks.

Examples of monomers which can be condensed to form amide linkages include: the natural L-amino acids, their enantiomers, and mixtures thereof (alpha-amino acids); conjugates of the natural amino acids with boron-containing groups or other groups of interest, e.g., lysine wherein the epsilon-amine function is used to link a boron-containing moiety, and/or a drug, chelator, enzyme, radionuclide carrier moiety, fluorescent marker, chromogen, nmr imaging agent or enhancer or the like; aspartic or glutamic acid wherein the beta- or gamma-carboxyl function is used to link one of the foregoing moieties; tyrosine, phenylalanine or histidine wherein the aromatic ring is substituted with such moieties; serine, threonine, tyrosine or hydroxyproline wherein the hydroxyl group is used to link the moieties, e.g., through an ether function; or cysteine wherein the thiol is used to form a thioether with another function of interest; other natural and synthetic amino acids with amine and carboxyl groups adjacent or farther removed from one another, and optionally conjugated to one or more of the foregoing types of moieties, examples of which are shown hereinafter; as well as diamines and dicarboxylic acids which can be linked by amide bonds in a "Nylon 66" fashion, the foregoing also optionally carrying additional functionality and/or being conjugated to the moieties mentioned above and further exemplified hereinafter. Examples of monomers which can form urea or thiourea functions include diamines, diisocyanates and diisothiocyanates.

It will be understood that the polymer chain can contain residues which do not contain boron, or which contain boron and other useful functions, e.g., a radionuclide, especially I-123, I-125 or I-131, or functions such as chelators, chelates with metal ions, drugs, toxins, chromophores, chromogens, fluorescent markers, and the like. The chain may also incorporate intrachain brancher residues, about which more will be said hereinafter. Finally, the chain may incorporate residues whose primary purpose is to improve the solubility and/or separability of the resultant conjugate.

As presently envisioned, the PAUT addends according to the invention are most advantageously synthesized by using a Merrifield-type solid phase synthesis, e.g., one using one of the currently available automated protein synthesizers. The individual component amino acid, diamino or dicarboxylic acid, diisocyanate or diisothiocyanate building blocks, suitably protected where necessary with groups that can be removed selectively in the course of automated synthesis, will be prepared in advance and coupled in a preselected sequence according to the desired properties of the resultant polymer.

Solid phase peptide synthesis is well known in the art, and the types of solid supports, protecting groups and coupling reactions used with the various naturally occurring amino acids are well documented, e.g., in Garland et al., "Biochemical Aspects of Reactions on Solid Supports", Chapter 3, pp 111-162, Stark, Ed. (Academic Press, New York, 1971); and Stewart et al., "Solid Phase Peptide Synthesis" (Pierce Chemical Corp., Rockford, IL., 1984); and the many specific references therein, all of which are well known to those engaged in the synthesis of polyamides of defined sequence and structure.

These techniques are readily adapted to the synthesis of polyureas and/or polythioureas, and the foregoing linkages can also be incorporated in polypeptide chains by minor modification of the conventional process steps. The standard methods will be modified for use with some of the new building blocks described herein. To the extent that such modifications are not familiar to one of ordinary skill in the art of solid phase peptide synthesis, they will be described in more detail hereinafter. It will also be appreciated that conventional solution phase reactions may be used to synthesize the PAUT addends, but that the yield, uniformity and purity of the resultant polymer are likely to be significantly lower than those obtainable using a solid phase synthesis technique.

The following discussion will present a more detailed treatment of certain preferred embodiments of the invention to illustrate the methods and utility of the generic invention, without limiting the scope thereof. In light of this discussion, it will become readily apparent how the invention can be practiced to achieve other embodiments.

It will be useful at this juncture to discuss boron cage compounds in a general way, to lay the groundwork for their use in synthesizing building blocks containing these compounds. The reader is referred to general references in this field for most of the reactions to be discussed hereinafter, the best and most comprehensive reference being Muetterties et al., "Polyhedral Boranes", (Dekker, New York, 1968); Muetterties, Ed., "Boron Hydride Chemistry", (Academic Press, New York, 1975); and Grimes, "Carboranes", (Academic Press, New York, 1970). These references contain copious bibliographies on specific topics within the broad subject range.

The most common and readily available kinds of boron cage compounds are the carboranes, especially the isomers of dicarba-closo-dodecaborane, having an icosahedral cage structure, and represented hereinafter by the symbol "H—{DB}—H". This cage compound can have any of three isomeric structures, viz., 1,2-, 1,7-, and 1,12-, wherein the two carbon atoms are on adjacent vertices, vertices separated by one boron atom, or vertices separated by two boron atoms (opposite poles) of the icosahedron, respectively. The symbol "H—{DB}—H" will refer to any of these three isomers, each of which can be used for nearly all of the reactions shown herein, except where noted.

The most common of the carborane cage compounds, and the most useful for further elaboration, is the 1,2-dicarba-closo-dodecaborane, which is readily synthesized by the classic reaction of an acetylene with $B_{10}H_{14}$. For example, 1-phenyl-1,2-dicarba-closo-dodecaborane is made by reacting phenylacetylene with $B_{10}H_{14}$, in acetonitrile solution, and is denoted by the symbol, H—{DB}—$C_6H_5$. A further useful property of these carboranes is their relative inertness to the conditions for many common organic reactions, e.g., aromatic halogenation, aromatic nitration, hydride reduction, catalytic hydrogenation, alkylation, acylation and the like. The carboranes can be converted to anions with one less boron vertex, by reaction with strong base, e.g., ethoxide, in protonic solvents, e.g., ethanol. They are also sensitive to primary and secondary amines, but not tertiary amines.

The structures of 1,2-dicarba-closo-dodecaborane and three cage borane carborane anions are shown below.

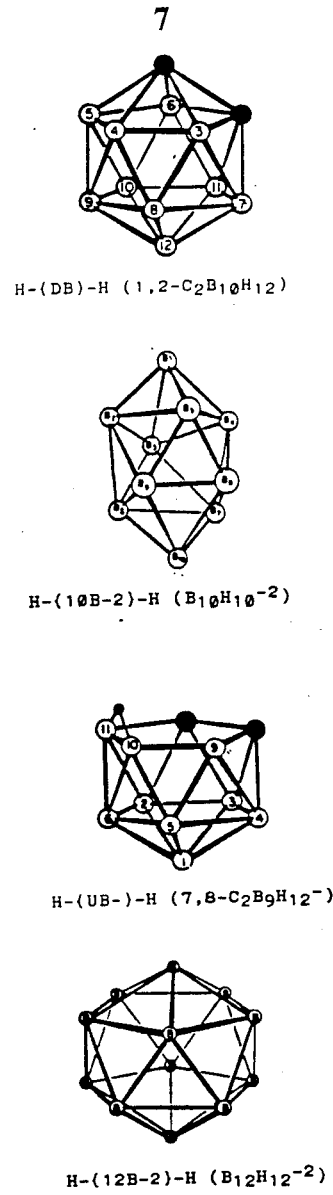

H—(DB)—H (1,2-C$_2$B$_{10}$H$_{12}$)

H—(10B-2)—H (B$_{10}$H$_{10}^{-2}$)

H—(UB—)—H (7,8-C$_2$B$_9$H$_{12}^-$)

H—(12B-2)—H (B$_{12}$H$_{12}^{-2}$)

○ BH  ● CH  • H

Conversions of the three isomeric dicarba-closo-dodecaboranes to their respective corresponding dicarba-nido-undecaborane anions, by reaction with base, is shown below.

closo—1,2—H—{DB}—H→nido—7,8—H—{UB—}—H closo—1,7—H—{DB}—H→nido—7,9—H—{UB—}—H closo—1,12—H—{DB}—H→no reaction closo—1,12—H—{DB}—H→nido—2,9—H—{UB—}—H The nido carborane anions shown above are denoted hereinafter by the symbol "H—{UB—}—H", representing a dicarba-nido-undecaborane monoanion.

Other readily available borane cages include the icosahedral closo-dodecaborane ($B_{12}H_{12}^{-2}$) dianion, hereinafter denoted by the symbol "H—{12B—2}—H", or the hexadecahedral closo-decaborane ($B_{10}H_{10}^{-2}$) dianion, hereinafter denoted by the symbol "H—{10B—2-}—H", whose structures are shown above. These can by modified to facilitate attachment to PAUT chains. Other less available borane and carborane cage compounds include carba-closo-dodecaboranes, lower boranes having, e.g., 6–9 and 11 boron atoms in the cage, heteroboranes, metalloboranes, and metallocarboranes. The metalloboranes are known, and their chemistry is described by Leyden et al, *J. Am. Chem. Soc.*, 100, 3758 (1978). The other classes of boron cage compounds are relatively rare, although known, and are described in the above-cited Muetterties references. The metallocarboranes, about which not a great deal of organic chemistry is known, are potentially of considerable use in the invention, as will be shown hereinafter.

Illustrative of one type of born containing antibody conjugate according to the present invention is the class wherein, in the formula Ab—(lr—PAUT)n, the polymer moiety, PAUT, is a polypeptide having the formula —(NH—Q—CO—)—OH, wherein each NH—Q—CO is a residue derived from (i.e., resulting from condensation of) a natural alpha-L-amino acid, or its enantiomer, or a mixture thereof, or a residue derived from an amino acid having the amine and carboxyl groups more remote than geminal, a plurality of which amino acids have a pendant amine, carboxyl, hydroxyl or thiol to which is bound a carborane-containing group, or a carborane to which are linked an amine and a carboxyl, optionally in positions more remote than geminally. Specific representative examples of carborane-linked amino acids, NH$_2$—Q—COOH from which such residues can be derived include, but are not limited to, those having the formula 1-14:

| | |
|---|---|
| H—{DB}—C$_6$H$_4$NHC(S)NH(CH$_2$)$_4$CH(NH$_2$)COOH | 1 |
| H—{DB}—(CH$_2$)$_3$C(O)NH(CH$_2$)$_4$CH(NH$_2$)COOH | 2 |
| H—{DB}—C$_2$ $_6$H$_4$NHC(S)OCH$_2$CH(NH$_2$)COOH | 3 |
| H—{DB}—C$_6$H$_4$NHC(O)(CH$_2$)$_2$CH(NH$_2$)COOH | 4 |
| M$^+$ H—{UB—}—C$_6$H$_4$NHC(S)NH(CH$_2$)$_4$CH(NH$_2$)COOH | 5 |
| M$^+$ H—{IUB—}—C$_6$H$_4$NHC(S)NH(CH$_2$)$_4$CH(NH$_2$)COOH | 6 |
| M$^+$ H—{UB—}—(CH$_2$)$_4$C(O)NH(CH$_2$)$_4$CH(NH$_2$)COOH | 7 |
| H—{DB}—C$_6$H$_4$N=N—(OH)C$_6$H$_3$CH$_2$CH(NH$_2$)COOH | 8 |
| H—{DB}—(CH$_2$)$_3$S(CH$_2$)$_2$CH(NH$_2$)COOH | 9 |
| H—{DB}—(CH$_2$)$_3$OC$_6$H$_4$CH$_2$CH(NH$_2$)COOH | 10 |
| H—{DB}—(CH$_2$)$_3$CH(NH$_2$)COOH | 11 |
| M$^+$ H—{UB—}—(CH$_2$)$_4$CH(NH$_2$)COOH | 12 |
| H$_2$N(CH$_2$)$_3$—{DB}—(CH$_2$)COOH | 13 |
| M$^+$ H$_2$N(CH$_2$)$_3$—{UB—}—(CH$_2$)$_3$COOH | 14 |

The iodo-substituted ion in compound 6 has one BH vertex replaced by a BI in the cage structure, and is denoted by the symbol "H—{IUB—}—H. M$^+$ in the formulas for compounds 5, 6, 7, 12 and 14 represents one equivalent of a convenient cation, e.g., an alkali metal, especially Na$^+$ and K$^+$, an alkali earth metal, especially Mg$^{+2}$ and Ca$^{+2}$ or a quaternary ammonium ion, especially (CH$_3$)$_4$N$^+$ and the like.

As noted above, the synthesis of linker peptides according to the invention can be achieved by conventional non-automated peptide synthesis routes which are lengthy, tedious and not easily applied to the rapid synthesis of many different members of a new class of peptides containing 2–50 amino acid residues. Indeed, the number of separation and purification steps required in non-automated synthesis makes the method unattractive from the viewpoint of time spent, synthesis control and quantity of peptide produced. In order to make gross, as well as finely tuned, adjustments in peptide linker sequences, and at the same time provide a sufficiently high throughput of material, it is preferable to use a Merrifield-type automated peptide synthesis machine, e.g., the Beckman Instruments 990 Peptide Synthesizer, and an associated Beckman 340 Series HPLC peptide purification system for the detection and separation of faulty peptide products formed during linker peptide synthesis.

Reagent chemicals such as amine-protected and/or carboxyl-protected amino acids are commercially available and generally usable without prior purification. Amino- and carboxyl-protected derivatives of B-10-containing amino acids or amino acid coupling reagents are new compounds which, after preliminary testing, are preferably prepared with Boron-10-enriched reagents for linker peptide synthesis and synthesis of linker-conjugated antibody for neutron irradiation therapy protocols.

The bonding of boron to a linker peptide may be accomplished in several ways, e.g., by using an amino acid containing a boron moiety integral to its structure, or by attaching a boron-containing moiety to a functional group on a side-chain of an amino acid. As an example of the former approach, synthesis of a bifunctional carborane derivative having an amino group on one arm attached to the cage and a carboxyl group attached to a second arm would allow the cage to be incorporated within the linker peptide chain. Acylation of the epsilon—$NH_2$ group in lysine using a carborane-containing carboxylic acid would provide an example of the latter tactic. One could also incorporate boron by both methods simultaneously.

A second factor to be considered is the charge type presented to the linker peptide molecule by the boron-containing residue. Electrically neutral carborane derivatives containing the hydrophobic icosahedral —{DB}— substituent (derivatization at carborane C-atoms) are advantageously used in the presence of strongly hydrophilic groups or replaced altogether by the related anionic —{UD—}— group, which has been incorporated in antibody conjugates and renders them significantly more water soluble (e.g., as $Na^+$ salts. In general, the desired anionic —{UD—}— species can readily be formed from the corresponding neutral —{DB}— icosahedral intermediate. The anionic carboranes are introduced during conjugating reagents which are themselves rendered more water soluble and often more compatible with the reaction medium.

Other charged boron-containing building blocks are available which made use of simple functional groups attached to the H—{12B—2}—H dianion (H—{12B—2}—SH is an example), or to the H—{10B—2}—H dianion. Such reagents are less adaptable in synthesis than similar carborane species since the polyhedral borane cages provide their own characteristic reactions reflecting strong electron-releasing properties and organic reactions often proceed in an unpredictable fashion.

The reagents used in the selected peptide syntheses must be compatible with the boron-containing species employed in linker synthesis. The H—{DB}—H icosahedral cage and its C-substituted derivatives are sensibly inert to chemical reagents except strong bases in the presence of an available proton source ($OH^-$/ethanol or certain primary and secondary amines). The generation of bases under conditions which occur during routine peptide sythesis, such as terminal —$NH_2$ groups, would not be important since the amino groups, when available, are sterically substantially inaccessible to neutral —{DB}— groups in the growing peptide chain and the amine reaction is normally slow.

On the other hand, the 11-vertex carborane anion —{UB—}—, in its derivatives, functions as an anion derived from a very strong acid ($C_2B_9H_{13}$). This anion is reversibly protonated with strong acids in nonaqueous media and is inert toward reagents other than reactive electrophiles. As an example, radioiodination of the —{UB—}— cage is used as a means of radiolabeling compound 15 to form protein conjugation reagent 16, according to the following equation.

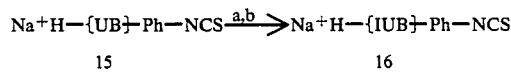

$$Na^+H-\{UB\}-Ph-NCS \xrightarrow{a,b} Na^+H-\{IUB\}-Ph-NCS$$
$$\quad\quad\quad 15 \quad\quad\quad\quad\quad\quad\quad\quad\quad 16$$

(a) Chloramine-T/NaI-125
(b) $Na_2S_2O_5$

Note that reagent 15 is prepared from the anionic aminophenyl derivative by reaction with thiophosgene, $CSCl_2$. Consequently, no serious difficulty is expected in the utilization of reagents based upon the H—{DB}—H and H—{UB—}—H carborane cages in automated linker peptide syntheses.

Attractive boron-containing reagents for attachment to side-chains of amino acids would include compounds for alkylation, acylation, amidation, carbamation/ureidation, thiocarbamation/thioureidation and diazonium coupling. They could bear uncharged/hydrophobic groups, e.g., —{DB}—, or charged/hydrophilic groups, e.g., —{UB—}—.

Alkylation could be effected, e.g., on the thiol or sulfide groups of cysteine or methionine, on the hydroxyl groups of serine, threonine, hydroxyproline, hydroxylysine or tyrosine, or on the amine groups of lysine or histidine. Acylation could be effected on the epsilon-amine group of lysine or on the aromatic amine group of histidine. It is normally considered disadvantageous to use conjugates linked with ester functions, since they are often readily cleaved by the many esterases in the blood and tissues. Nevertheless, it will be apparent to the skilled worker that the hydroxyl groups of the aforementioned amino acids can be acylated to form esters with boron-containing acylating agents.

Carbamation/ureidation and thiocarbamation/thioureidation are readily effected by reacting pendant amine and/or hydroxyl groups with boron-containing reagents bearing isocyanate or isothiocyanate functions. Amidation can be effected by reaction of pendant amine functions with boron-containing carboxylic acids, or by reacting pendant carboxyl groups such as those on aspartic or glutamic acids with boron-containing amines, conveniently by using a condensing agent, e.g., dichlorohexylcarbodiimide (DCC). Diazonium coupling is effected by reaction of a diazonium salt, prepared by diazotization of a boron-containing amine, e.g., by reaction of the amine with sodium nitrate and acid, with an aromatic amino acid, e.g., tyrosine, histidine or phenylalanine.

Boron-containing alkylating agents 17-21, bearing carborane or borane anion groups, can be synthesized by the following pathways, which are meant to be illustrative of the various methods available, and which can be modified and adapted to produce analogous reagents with minor structural differences. Alkylating agents containing carborane anion groups can be most easily produced by base treatment of the corresponding carborane precursors at convenient branch points in their synthesis. Metallocarboranes can be made by adapting syntheses for producing analogous acylating agents, but these are somewhat cumbersome.

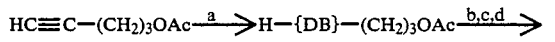

H—{DB}—(CH₂)₃I

17

(a) B₁₀H₁₄/acetonitrile, reflux (b) LiAlH₄/ether, or aqueous acid hydrolysis (OAc——→OH)

(c) toluenesulfonyl chloride/pyridine (OH——→OTs)

(d) sodium iodide/acetone (OTs——→I)

Zakharkin et al., Zh. Obshch. Khim., 35. 2160)1965)

It will be apparent that either iodide 17 or its precursor tosylate can be used for alkylation of amines, hydroxyls or phenoxides and thiols. Moreover, the chain length can be varied merely by using a starting acetylene of shorter or longer chain length, or by homologating the product by, e.g., conversion of the iodide to a Grignard reagent, followed by addition to formaldehyde, other aldehydes, ketones or epoxides, or the like. Similarly, alkyl-substituted acetylenes can be used initially, as can acetylenes substituted with other groups which do not interfere with subsequent reactions, e.g., ether, aryl, nitro, cyano or fluoro groups, and the like.

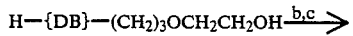

18

(a) ethylene oxide, BF₃ (separate oligomers)

(b) TsCl/pyridine (OH——→OTs)

(c) NaI/acetone (OTs——→I)

The length of the chain in the starting acetylenic alcohol, which is an intermediate in the synthesis of 17, can readily be varied as noted above. The resultant alcohol can be homologated, and/or a different epoxide can be used to make the ether-alcohol, to achieve variant structures of this general type.

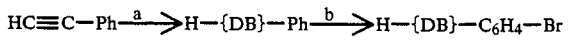

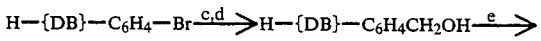

-continued

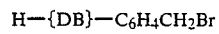

19

(a) B₁₀H₁₄/acetonitrile, reflux
(b) Br₂
(c) Mg/ether
(d) CH₂O
(e) SOBr₂

The benzyl alcohol intermediate in the above scheme can be prepared by hydride reduction of the corresponding benzoic acid, H—{DB}—C₆H₄COOH, whose preparation is shown hereinafter. Further variants of the general class of alkylating agents represented by compound 19 can be readily envisioned, e.g., ring-substituted derivatives having alkyl, aryl, fluoro, alkoxy, aryloxy, nitro groups, and the like; substituents at the benzylic carbon; and/or homologs and isomers thereof.

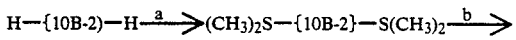

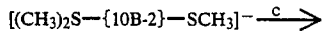

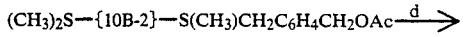

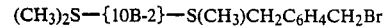

20

(a) dimethylsulfoxide (DMSO)/H⁺
(b) potassium phthalimide, heat
(c) BrCH₂C₆H₄CH₂OAc
(d) HBr
Sneath, et al., J. Med. Chem., 17, 796(1974)

The tosylate corresponding to bromide 20 can be readily made by base-catalyzed hydrolysis of the acetate intermediate above, and reaction of the resultant alcohol with TsCl/pyridine. Structural and isomeric variants of bromide 20 are easily envisioned by the skilled artisan, and these include but are not limited to ring isomers, alkyl, aryl, alkoxy, aryloxy, fluoro, nitro substituents, other alkyl, aryl, aralkyl and aralkyl substituents on the sulfonium group, and the like.

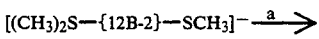

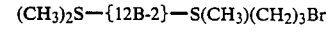

(a) Br(CH₂)₂COOH
(b) LiAlH₄
(c) PBr₃ or SOBr₂ (or TsCl/py for tosylate)
Sneath, et al., J. Med. Chem., 17, 796(1974)

The starting material for this sequence is obtained analogously to the corresponding intermediate in the previous sequence, except that H—{12B—2}—H is used instead of H—{10B—2}—H to react with the DMSO. It will be apparent that other haloacids and/or esters can be used instead of the beta-bromopropionate, e.g., alpha-bromoacetate or other alpha-haloalkanoic acids of esters, methyl alpha-bromophenylacetate or other alpha-haloalkanoic acids or esters, gamma-haloacids or esters, delta-haloacids or esters, and the like.

Representative examples of the use of these alkylating agents to produce amino acid building blocks for peptide synthesis follow.

It is seen that alkylating agent 17 can be used to convert the thiol of cysteine of a thioether, resulting in compound 9. (The skilled artisan will recognize that the cysteine will normally be in the form of an N- and C-protected derivative, and that one or the other of the protecting groups will normally be removed by conventional means before the boron-containing amino acid is joined to a growing peptide chain under standard solid phase reaction conditions.)

Similarly, compound 17 can alkylate the phenolic oxygen of a suitably protected tyrosine, resulting in the production of boron-containing amino acid 10, again suitably protected. In an analgous fashion, alkylating agents 18–21 can be used to attach other types of boron cage structures to pendant amine, hydroxyl or thiol functions of suitably protected amino acids. In addition, these alkylating agents and their precursors and/or derivatives are also useful as intermediates in various classical amino acid synthesis schemes, examples of which will be shown hereinafter.

Representative acylating agents 22–29, incorporating carborane, carborane anion and borane anion moities, are shown below, together with illustrative synthetic sequences by which they can be produced. Again, it will be appreciated that many structural and isomeric variants of these compounds may be made by varying the structure of the reactants and by minor modifications of the reaction conditions in ways that are familiar to the skilled artisan. The types of permissible substitution and/or isomerization correspond to those mentioned above for synthesis of related structures.

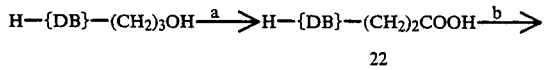

22

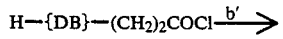

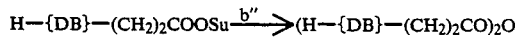

(a) chromic acid
(b) thionyl chloride
(b') N—hydroxysuccinimide (HOSu)/DCC
(b'') acetic anhydride Acid 22 can be condensed with a pendant amine group, e.g., on a lysine residue suitably protected at the alpha-amino and -carboxyl termini, using DCC as an illustrative carbodiimide-type condensing agent. More rapid condensation, which can dispense with the need for a condensing agent, can be effected with any of the activated acid derivatives shown, viz., the acid chloride, the N-hydroxysuccinimide ester or the anhydride, among other known carboxyl derivatives.

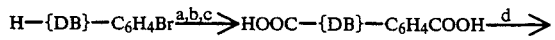

H—{DB}—C₆H₄COOH
23

(a) butyl lithium (lithiates phenyl and removes carborane methylene proton)
(b) carbon dioxide
(c) acidification
(d) ethanol reflux (decarboxylates carborane)
Hawthorne et al., J. Am. Chem. Soc., 87, 4746(1965)

An intermediate from the synthesis of compound 19 is the starting point for the foregoing sequence, which readily produces 1,2- and 1,7-carboranyl-p-benzoic acids. These can be converted to activated carboxyl derivatives by analogous methods to those used on compound 22.

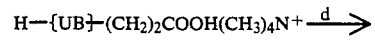

$Na^+H—\{UB\}—(CH_2)_2COOSu$
24

(a) ethoxide/ethanol (1,2- and 1,7-dicarba-closododecaboranes⟶corresponding nido-undecaboranes, 1,12-isomer uses Busby et al. method shown earlier)
(b) acidify, e.g., with HCl
(c) (CH₃)₄NCl
(d) HOSu/DCC
(e) ion exchange
(f) lyophylization
Hawthorne et al., J. Am. Chem. Soc., 90, 862(1968).

Any of the isomeric carboranes, e.g., carboranyl propionic acid 22 illustrated above, can be degraded with base to the corresponding anion with one less boron vertex, by the procedures shown above, acidified, and the product isolated as the quaternary ammonium ion. The OSu ester is conveniently prepared, and can be optionally converted to the sodium salt by ion exchange and (also optional) lyophylization.

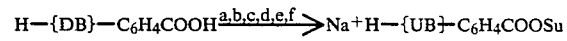

25

(a) ethoxide/ethanol (1,2- and 1,7-dicarba-closododecaboranes⟶corresp. nido-undecaboranes;

1,12-isomer uses Busby et al. method shown earlier)
(b) acidify, e.g., with HCl
(c) (CH₃)₄NCl
(d) HOSu/DCC
(e) ion exchange
(f) lyophylization Carboxylic acid 23 can be degraded by a similar sequence and converted to the activated carborane anion acylating agent 25.

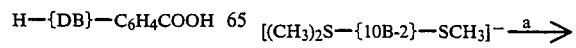

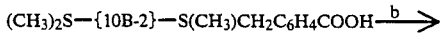

-continued

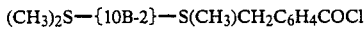
26

(a) BrCH₂C₆H₄COOH
(b) SOCl₂
Sneath et al., *J. Med. Chem.*, 19, 1920(1976)

An intermediate in the synthesis of compound 20 can be S-alkylated with the readily available alpha-bromotoluic acid to produce a neutral toluic acid derivative, which can be converted to acid chloride 26. The reaction sequence can be effected with 1,6- or 1,10-decarboranyl and with 1,12-dodecaboranyl starting materials. It will be appreciated that acid chloride 26 is only one of several possible activated acid derivatives useful for acylation under mild conditions, and that the acid itself can be used for acylation, e.g., with an amine, in the presence of DCC.

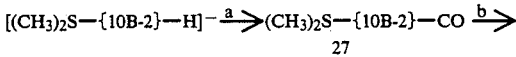
27

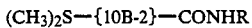
a (COCl)₂
b RNH₂ (e.g., lysine epsilon-amino group)
Wong et al., *J. Med. Chem.*, 17, 785(1974)
Muetterties et al., "Polyhedral Boranes", op. cit.

The monoaddition product of closo-decarborane dianion and DMSO reacts with oxaloyl chloride to form 1,6-acylium derivative 27, which is reactive with amines to form amide linkages.

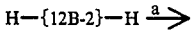

[H—{12B-2}—CO]⁻ + OC—{12B-2}—CO
 28                       29 a CO/H⁺, pressure
Muetterties et al., "Polyhedral Boranes", op. cit.

Closo-dodecaborane dianion adds carbon monoxide to form a monoacylium or 1,7- and 1,12-diacylium derivatives, both of which react with amines to form amides similarly to compound 27.

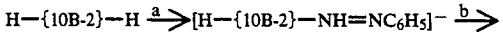

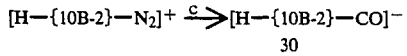
30 a C₆H₅N₂⁺BF₄⁻
b acetonitrile, reflux
c CO, pressure, 120° C.
Leyden et al., *Inorg. Chem.*, 14, 2444(1975)
Hawthorne et al., *J. Am. Chem. Soc.*, 87, 2366(1965)

Closo-decarborane dianion reacts with phenyldiazonium tetrafluoroborate to form an intermediate which loses benzene upon heating, resulting in a diazonium derivative which can be carbonylated under pressure, with loss of nitrogen. The resultant acylium compound, 30, reacts with amines to form amides.

Metallocarborane reagents for modifications of amino acid side chains, or for direct incorporation into PAUTs, can be prepared using reactions which are known to those skilled in the art of boron chemistry. Useful general references for the types of reactions envisaged include, e.g., Muetterties, Ed., "Boron Hydride Chemistry", op. cit., Chapter 11; Hawthorne et al., *Science*, 78, 462 (1972); Hawthorne et al., *Accts. Chem. Res.*, 1, 281 (1986); and references cited therein. The following examples and reaction sequences are, therefore, merely illustrative of the types of compounds and the types of metal ions which can be incorporated into addends for preparing antibody conjugates. Nearly every type of metal ion has been incorporated or can be incorporated into these metallocarboranes, so that the use of Co(III) as a model is clearly not limiting and metals such as In(III)-111, Ga(III)-67, Gd(III), Y(III)-90, and the like can be substituted therefor. The complexes are of the "sandwich" type similar to ferrocenes and can incorporate substituted or unsubstituted cyclopentadienide rings, hereafter denoted by the symbol "{CPD—}", as well as {UB-2} moieties, prepared by treatment of {UB—} rings with strong base, e.g., NaH, to remove the bridge hydrogen and product the "dicarbollide" dianion.

The cyclopentadienide anion is conventionally produced by cracking cyclopentadiene dimer and reacting the monomer with base, e.g., NaH. The carborane dianion is normally produced by treating the monoanion with strong base, e.g., NaH, to remove the bridge hydrogen. It is common for several isomers to be produced by this procedure, and these may be separated if desired or used as a mixture. Either anion may bear a substituent for later attachment to an amino acid side chain, substituted cyclopentadienides being readily prepared, and substituted dicarbollides having already been shown, either as such or as their monoanion precursors.

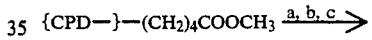

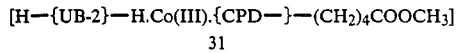
31 a H—{UB-2}—H solution in tetrahydrofuran(THF)
b CoCl₂ in THF
c workup in air (Co(II)→Co(III))

It will be recognized that the ester function in compound 31 can be readily hydrolyzed to a carboxylic acid, which can then be converted to an acid halide, anhydride or OSu ester by methods already shown hereinabove. Alternatively, a Schmidt reaction, or analogous degradation, can convert the acid or ester to an isocyanate, which can be further hydrolyzed to an amine. Thus, the metallocarborane sandwich complex can be linked to amino acid side chains by a variety of methods and can form a variety of bonds thereto.

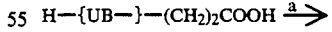

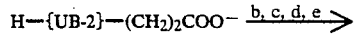

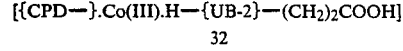
32 a NaH/THF
b {CPD—}/THF
c CoCl₂/THF
d workup in air
e acidify

The starting carborane anion and the intermediate dicarbollide dianion are both chiral, and can be used as pure enantiomers or as a mixture, e.g., a racemic mixture. Again, the acid function of compound 32 can be converted to other convenient groups for acylation of formation of other linking groups. In this and the other reactions for formation of metallocarboranes with two different groups forming the sandwich, it is possible to form side products with two of the same ligands bound to the metal. These side products often can also be used as addends and/or as chain forming reagents, as will be seen hereinafter.

By using the same procedure as above, except that a dicarbollide dianion, H—{UB-2}—H, is added in step (b), instead of the {CPD—} anion, compound 33 can be prepared, having the structure;

[H—{UB-2}—H.Co(III).H—{UB-2}—(CH₂)₂COOH]⁻
33

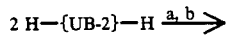

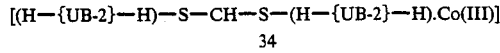
34 a CoCl₂/THF
b workup in air
c CS₂/AlCl₃
Frances et al., Inorg. Chem., 10, 594(1971)

The foregoing reference also discloses a bridged sandwich complex with an —OCHO— bridge, wherein the carbon atom of the bridge also bears a positive charge. It will be understood that the dicarbollide groups are bound to sulfur (or oxygen) at boron atoms and not at carbon atoms. The metal ion (Co(III) in these examples) is sandwiched between the dicarbollide groups which, in this bridged case, cannot rotate freely with respect to one another as they can in the unbridged sandwich complexes shown above. The electrophilic carbon atom of the bridge can accept an electron pair from a nucleophile, e.g., an amine group or a malonic ester anion, and can thereby become attached to an amino acid side chain. Thus, for example, reaction of 34 with the sodium salt of diethyl malonate, followed by hydrolysis and decarboxylation of the malonic acid adduct, will produce a bridged sandwich complex with an acetic acid group on the carbon atom of the bridge. This derivative can be condensed with an amine group or an amino acid side chain, e.g., lysine, or it can be converted to on of the activated acid derivatives mentioned above or to an amine, an isocyanate or an isothiocyanate by conventional transformations.

It will also be apparent that other linking functions can be substituted for the alkanoyl group shown in the above examples, e.g., a benzoic acid function or other alkyl, aryl, cycloalkyl, alkaryl or aralkyl carboxylic acid or acid precursor. Various substituents can also be present, analogously to earlier examples, provided they do not interfere with the reactions being effected.

Carbamation, thiocarbamation, ureidation, thioureidation and diazonium coupling are all related, in that they can all be effected using a common amine precursor. The following examples will illustrate this point, and show how other groups of addends can be produced which are capable of reacting with pendant hydroxyl or amine functions to form carbamate/thiocarbamate or urea/thiourea functions, or which can be diazotized and reacted with aromatic residues to form diazo adducts.

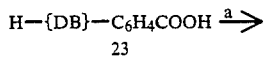
23

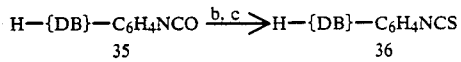
35            36 a HN₃ (Schmidt Reaction)
b H₃O⁺
c CSCl₂

Compound 23 is converted to the next lower isocyanate, 35, in a Schmidt Reaction. The isocyanate can be reacted with a pendant amine or hydroxyl group an an amino acid residue to produce the corresponding urea or carbamate. Alternatively, the isocyanate can be hydrolyzed to the amine, which can then be converted, by reaction with thiophosgene in acetone, at low temperature, to the isothiocyanate, 36, in good yield. Isothiocyanate 36 can be reacted with pendant amine and hydroxyl groups of amino acid residues to produce thioureas and thiocarbamates. For example, reaction of 36 with (suitably protected) lysine, at its side chain amine, produces compound 1 (also protected). Similarly, reaction of 36 with the side chain hydroxyl of (suitably protected) serine produces (protected) compound 3.

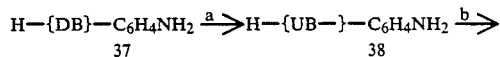
37                  38

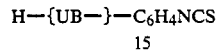
15 a ethoxide/ethanol
b CSCl₂

The amine, 37, produced by hydrolysis of compound 35, is readily converted to the corresponding carborane anion 38, which can then be reacted with thiophosgene to produce the isothiocyanate 15. This compound is used to form thiocarbamate or thiourea derivatives of pendant hydroxyl or amine functions of amino acid residues, e.g., formation of compound 5 by reaction with (suitably protected) lysine.

As noted above, compound 15, in the form of a suitable metal or quaternary ammonium salt, can be iodinated, by reaction with NaI and Cloramine-T in buffered aqueous solution, on the carborane cage rather than the benzene ring, a reaction which is of considerable interest for the eventual synthesis of antibodies containing both a radiolabel, e.g., I-125, I-131, or I-123, and boron atoms for in vitro diagnostic use and for in vivo diagnostic and/or therapeutic use, particularly for the targeted thermal neutron activated therapeutic methods for treating tumors and pathological lesions disclosed in the above-reference Goldenberg patents and patent applications. The resultant iodocarborane, 16, can be used to incorporate both radioiodine and B-10 atoms in the linker peptide by, e.g., reaction with the epsilon-amine of alpha-protected lysine, e.g., to produce compound 6.

With the use or I-125, radiolabeled carborane can be covalently attached to antibody and the efficiency of coupling, as well as the distribution of labeled antibody in tissues, can be accurately assayed. Use of I-131 or I-123 permits labeling with radionuclides of interest for in vivo diagnostic and therapeutic procedures.

Loss of iodine label by enzymatic dehalogenation may be a disadvantage attendant upon use of antibodies directly radioiodinated using, e.g., the Chloramine-T procedure. Most of the iodine is probably bound to the aromatic ring of tyrosine residues on the antibody. The carborane anion, such as in compound 6, is a poor substrate for dehalogenases and markedly reduces loss of radiolabel due to dehalogenation in vivo.

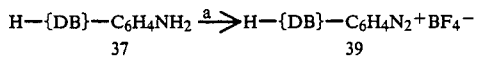

37          39 a HNO$_2$/HBF$_4$
Hawthorne et al., J. Med. Chem., 15, 449(1972)

Diazotization of amine 37 produces diazonium salt 39, which can be used to add to the phenol ring of a (suitably protected) tyrosine residue to produce (protected) compound 8.

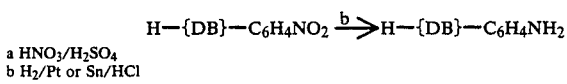

a HNO$_3$/H$_2$SO$_4$
b H$_2$/Pt or Sn/HCl

An alternative method for obtaining the aromatic amine 37 is nitration of the benzene ring of a phenyl-carba-closo-dodecaborane, followed by conventional reduction of the nitro group. The amine can be transformed with thiophosgene to an isothiocyanate or with phosgene to an isocyanate.

It will be appreciated that that carboxylic acids mentioned above, as well as the structural variants thereof, can be converted to amines, which can themselves be condensed with pendant carboxyl groups of amino acids such as aspartic or glutamic acids. The amines can be further converted to isocyanates and diazonium salts (normally only the aryldiazonium salts are sufficiently stable for coupling with an amino acid).

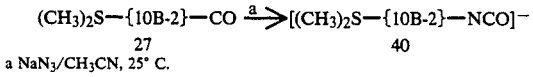

27          40 a NaN$_3$/CH$_3$CN, 25° C.

Acylium borane 27 can be converted to the corresponding isocyanate by a reaction that resembles a Schmidt Reaction. This reaction can also be performed on compounds 28 and 30 above, with similar results.

The many examples illustrating some of the types of side chain modifying groups which can be envisioned are not intended to be exhaustive, but representative of the vast number of possible groups of this sort which are included within the scope of the present invention. It will be appreciated that, in any of the foregoing side chain-modifying reagents, the boron-containing moiety can be replaced by a chelator, a drug, a toxin, a fluorescent group or the like useful addend, which can thereby be incorporated into the PAUT and eventually conjugated to the antibody.

Another type of residue for incorporation into PAUT according to the present invention is an amino acid which is not a side chain-modified or derivatized amino acid, but rather, a synthetic, "devised" amino acid which incorporates a boron cage directly into an amino acid, i.e., through a carbon-carbon bond. For convenience, these are grouped into two categories: the side chain cage type; and the in-chain cage type. Representative examples of each type of residue will be given, including residues with a carborane, carborane anion, borane anion and metallocarborane, whenever available.

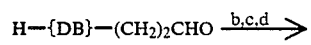

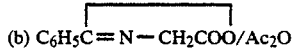

11

(a) LiHAl(OEt)$_3$ (b) C$_6$H$_5$C≡N—CH$_2$COO/Ac$_2$O (c) H$_2$/Pt
(d) H$_3$O$^+$

The acid chloride derived from 22 is reduced to the corresponding aldehyde with lithium triethoxyaluminum hydride. The aldehyde is condensed with the cyclized form of N-benzoylglycine, in an aldol-type condensation, followed by dehydration with acetic anhydride. The double bond is hydrogenated to produce a new chiral center, and the cyclized ring is hydrolyzed to form an alpha-amino acid. If the hydrogenation is effected with a chiral catalyst, either the L- or D-enantiomer can be selectively generated. Alternatively, the racemic acid can be separated into its component enantiomers by conventional means, involving formation of a salt with one enantiomer of a chiral base or acid, fractional crystallization, and recovery of the pure enantiomer. The amino acid can be reacted with a protecting reagent, e.g., t-butyl chloroformate (BOC—Cl) to form the N-BOC derivative for use in solid phase synthesis.

It will be appreciated that the foregoing method is quite general and can be adapted to the synthesis of a great number of other side chain amino acids via the corresponding carboxyl derivative. Similarly, Strecker Synthesis upon the intermediate aldehyde (reaction with KCN/NH$_4$Cl, followed by hydrolysis) will produce an amino acid with one less methylene in the chain, viz., H—{DB}—(CH$_2$)$_2$CH(NH$_2$)COOH.

Devised side chain amino acids with anionic boron cage groups can be simply prepared by reacting the corresponding carborane cage compounds with base. The resultant carborane anions are often chiral, and result in mixtures of enantiomers and diastereomers, which can all be conventionally separated. Compound 12 is an example of such a species, produced by treating the next higher homolog of compound 11 with ethoxide in ethanol.

Similarly, metallocarboranes such as 31 and 32, can be transformed into side chain boron-containing amino acids by converting their carboxyl groups into aldehyde groups by the foregoing procedure, and carrying out a Strecker Synthesis thereon, as shown above. The resultant mixture of chiral amino acids can be resolved. The product of this sequence on compound 31 will be a mixture of enantiomers, while the product from compound 32 will be two diastereomeric pairs of enantiomers. Since the carborane anion cage is itself chiral. Analogous transformations can be effected on compound 33 and the acetic acid adduct (from malonate addition) of compound 34.

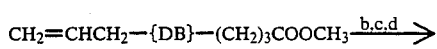

$NH_2(CH_2)_3-\{DB\}-(CH_2)_3COOH$

13

(a) $B_{10}H_{14}/CH_3CN$
(b) $B_2H_6$
(c) $H_2NOSO_3H$
(d) $H_3O^+$

A disubstituted acetylene, prepared by sequential alkylation of acetylide by allyl bromide and methyl gamma-bromobutyrate, is condensed with decaborane tetradecahydride to form the closo-carborane cage. Conventional hydroboration/amination, followed by hydrolysis of the ester, produces an amino acid having a boron cage in the chain which has the amine and carboxyl functions as chain termini. It will be understood that suitable protecting groups, e.g., BOC, will normally be introduced to prepare residues for automated solid phase peptide synthesis.

Analogously to earlier examples, compound 13 can be treated with ethoxide/ethanol to produce anionic boron cage compound 14. It will normally be convenient to isolate this compound as its tetramethylammonium salt.

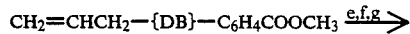

$NH_2(CH_2)_3-\{DB\}-C_6H_4COOH$

41

(a) butyl lithium (2 equivalents)/THF
(b) allyl bromide (2 equivalents)
(c) hydrolysis ($H_3O^+$, neutralize)
(d) diazomethane
(e) $B_2H_6$
(f) $H_2NOSO_3H$
(g) $H_3O^+$ Compound 23 can be transformed into an in-chain amino acid by alkylation with an allyl group at the remaining carbon vertex of the carborane, followed by conventional hydroboration/amination. By analogy to earlier procedures, treatment of compound 41 with ethoxide/ethanol will produce the corresponding amino acid, 42, with a nido-carborane anion cage. Also by analogy to earlier discussions, the many structural variants of carboxyl and amine compounds can be elaborated by similar schemes to in-chain amino acids.

Metallocarborane sandwich complexes with an amine terminus and a carboxyl terminus on opposite boron anion cages represent one illustration of the type of in-chain species envisioned for this type of boron-containing moiety. It will be apparent that in-chain anionic amino acids such as compound 42 can be further elaborated into metallocarboranes by reaction with strong base and combination with another dianion cage and a metal ion, using a procedure analogous to the following.

 (A)

 (B)

$A + B$ 

$[H-\{UB-2\}(CH_2)_2NH_2.Co(III).H-\{UB-2\}(CH_2)_2COOH]^-$

43

(a) NaH/THF (2 eqvts.)
(b) $CoCl_2$/THF
(c) workup in air, acidify

The amine anion used to generate Solution A can be produced from acid 22 by Schmidt Reaction, hydrolysis of the resultant isocyanate, and base treatment to generate the nido-carborane anion. Treatment of compound 22 with strong base directly produces the starting material for generation of Solution B. Each of these starting materials can be a mixture of enantiomers or a single enantiomer. Accordingly, the resultant sandwich complex can either be a single chiral product or a mixture of four enantiomeric or diasteriomeric products, which can be separated by conventional means or used as a mixture. It will also be appreciated that the reaction can produce byproducts, i.e., the complexes having an amine on both dicarbollide groups or having a carboxyl on both dicarbollide groups. These byproducts can be separated from the desired amino acid complexes by virtue of their differences in acidity/basicity, and they will be useful in other contexts, as will be shown hereinafter.

It is presently anticipated that synthesis of PAUTs from amino acid residues will be most conveniently effected by means of an automated solid phase peptide synthesizer. The first residue is normally attached to beads of a polymer resin, e.g., polystyrene, suitably functionalized to accept substitution of a carboxylate anion for a labile substituent, e.g., by halomethylation. Standard machine conditions ordinarily involve attachment of the C-terminal residue to the resin, e.g., by attack of its carboxylate on a benzylic carbon of a halomethylated polystyrene. The C-terminal residue and subsequently added residues have their alpha-amine functions protected by BOC groups, which are cleaved by $CF_3COOH$ in $CH_2Cl_2$ after each successive addition of a residue. Condensation of the deblocked N-terminus with the carboxyl group of the next (N-protected) residue is effected with DCC, and excess residue and DCC are washed out with triethylamine. The finished peptide is cleaved from the solid support with liquid HF.

For more sensitive residues, milder conditions can be used, e.g., the use of Bpoc ($-COOC(CH_3)_2-C_6-H_4-C_6H_5$) as an N-protecting group, which can be cleaved with dilute $CF_3COOH/CH_2Cl_2$, binding of the C-terminal group to the resin through a readily cleaved ether linkage, or use of a base-cleavable N-blocking group, e.g., the Fmoc (fluoroenyl-methoxycarbonyl) group, which can be cleaved by piperidine. Use of the latter protecting group must take cognizance of the fact that it will affect chains where a carborane cage is incorporated, since the piperidine will convert the carborane to its corresponding nido-anion. In certain cases, it may be useful to achieve this transformation in the course of peptide synthesis, rather thatn by earlier treatment of the residue with strong base.

The foregoing are merely suggestive of the procedures which will be familiar to one of ordinary skill in solid phase peptide synthesis, in view of the many excellent and comprehesive references generally available in the art, the Garland et al. and Stewart et al. references noted hereinabove being among the most useful. Once the sequence of amino acid residues is selected, it will normally be a routine matter to choose the proper protecting groups for the individual residues and to choose the proper automated conditions for their linkage.

Further structural variety may be achieved by the use of chain branchers, either at the beginning of a chain or at one or more intermediate points in the chain. These may be residues uniquely designed for this purpose or they may be natural or synthetic amino acids or other related functionally substituted groups which can serve the purpose of accepting branch chains or addends. Representative illustrations of the types of compounds envisioned will show the nature and scope of these components.

The simplest type of brancher is a natural amino acid with a pendant functional group, to which can be attached another preformed PAUT chain. For example, the epsilon-amino group of a lysine residue can be protected with a selectively cleavable group which survives cleavage of the BOC group, e.g., a benzyl group which can be hydrogenolyzed at a point when branching is desired, or e.g., a Bpoc group which can be cleaved without cleaving the chain-terminal N-BOC. In either case, the epsilon-amino group can be linked to a branch chain either prior to or subsequent to further elaboration of the trunk chain. Similarly, an aspartic or glutamic acid residue can be used as a brancher, protected by a selectively cleavable group.

The protecting group also can be cleaved either prior to or subsequent to chain extension of the trunk peptide.

Another type of brancher is a molecule of the general type $YG(X)_2$, wherein G is any central structure, Y is a function reactive with an antibody, and X is a more reactive function that will kinetically favor reaction with, e.g., the amine terminus of a growing polymer chain. As an illustration, such a brancher could be 3,5-di(bromocarbonyl)phenylisothiocyanate, wherein G is the benzene ring, Y is the NCS group, and each X is a COBr group. Branching could be effected as follows;

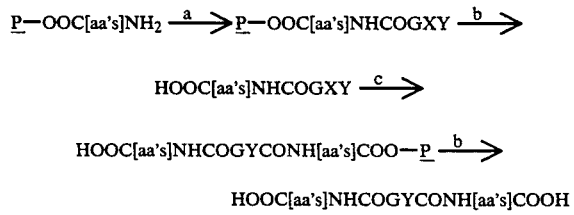

(a) $YG(X)_2$
(b) HF or $CF_3COOH$
(c) $H_2N \ldots COO—\underline{P}$

Here, a first completed polymer chain (deblocked) is reacted with an excess of the brancher, so that each amine terminus bears a brancher with one acyl bromide and one isothiocyanate. The intermediate is cleaved from the resin (P) and the free polymer is reacted with a second completed polymer bound at the C-terminus to resin. A kinetic preference for reaction with the acyl bromide over the isothiocyanate will result in linkage to form an amide bond. Cleavage again from the resin produces a group having two polymer chains attached to the phenylisothiocyanate by amide bonds, which can then be linked to antibody through the NCS group.

The foregoing examples are merely a suggestion of the manifold possibilities for branchers, which are limited only by the caveat that they have selectively reactive groups thereon which can react first with the terminus or a pendant group of a polymer chain and later with a pendant function on an antibody. Other variants within the scope of the present invention will be apparent to those of ordinary skill in this art.

It should be noted that another type of "brancher" can be used to link together two Fab or Fab' functions, using their free SH groups. This could be done by growing polymer chains and capping the terminal amines with an alkylating group, e.g., $COCH_2Br$, cleaving the C-terminal carboxyl from the resin, and reacting the cleaved polymer with p-phenylenediamine/DCC, to produce a longer joined polymer having a bromoacetamide at each end. This could then be reacted with Fab or Fab' fragments, under reducing conditions, to bridge the two fragments. A further option is to include yet a third function on the joining moiety to which additional functional groups can be added. A lysine with two BOC protecting groups on the two amine functions can be added to the end of a polymer chain still attached to the solid phase, the BOC groups cleaved, the two amines acylated with bromoacetyl chloride, and Fab/Fab' fragments reacted with the resultant polymer. Selective protective groups and sequential deblocking/acylation/alkylation with different Fab/Fab' fragments would produce a hybrid divalent immunoreactive agents. The possibility of multivalent hybrids should be recognized, using this technique. The resin-bound product can be cleaved and the C-terminal group further modified if desired.

Additional branching and capping groups will be disclosed hereinafter, in connection with methods of forming PAUTs using homodifunctional residues.

Although automated solid phase peptide synthesis effects great improvement in the production of defined sequenced polymers, the method still requires the use of protecting groups in each step, by virtue of the fact that both an amine and a carboxyl group are present in each residue to be linked. In contrast to McKearn et al., the object of the present invention is not necessarily to conjugate to an antibody a polypeptide made of natural amino acids. Accordingly, this invention envisages the use of homodifunctional residues to build PAUTs, preferably also on a solid phase, but without some of the inconvenience entailed by the use of amino acids as building blocks. The simplest such approach is the use of alternating diamine and diacid building blocks to produce a "nylon 66" type polymer. Another approach is to use diamines with diisocyanates and or/diisothiocyanates to form poly(urea/thiourea) chains, again in the "nylon 66" sense. It will be apparent that any combination of the foregoing can also be used. Moreover, this approach can be combined with the conventional approach, using amino acids, either for construction of the trunk PAUT, or for modification of side chains, branching or linking to particular types of functional groups. More specific representative illustrations of each of these approaches will be disclosed hereinbelow, although it will be appreciated by the ordinary skilled artisan that many other species can be envisaged, all of which fall within the clear scope of the invention.

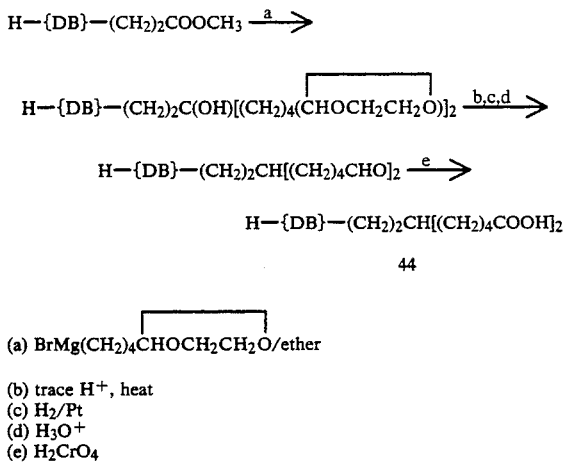

(a) BrMg(CH₂)₄CHOCH₂CH₂O/ether (b) trace H⁺, heat
(c) H₂/Pt
(d) H₃O⁺
(e) H₂CrO₄

Starting with the methyl ester of compound 22, Grignard reaction with 2 equivalents of the reagent poduced by reacting Mg with the ethylene acetal of 5-bromovaleraldehyde results in a tertiary alcohol. The alcohol can be dehydrated under mild conditions, and the resultant olefin is hydrogenated. Hydrolysis of the acetals and oxidation of the aldehyde groups to carboxyls completes the synthesis. It will be recalled that carboxyl groups can be converted to isocyanates by the Schmidt Reaction, and this can be done with the diacid to produce a diisocyanate. Similarly, hydrolysis of the isocyanates produces a diamine, which can be reacted with thiophosgene to give a diisothiocyanate. All of these homodifunctional residues will be useful in the ensuing techniques for chain formation.

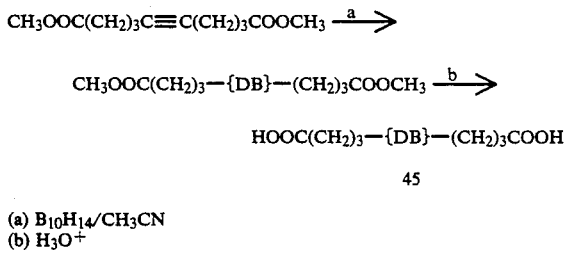

(a) B₁₀H₁₄/CH₃CN
(b) H₃O⁺

The disubstituted acetylene obtained by reaction of acetylide with two equivalents of methyl 4-bromobutyrate is then reacted with decaborane tetradecahydride to form a carborane cage in a now-familiar reaction. The resultant diester is hydrolyzed to the diacid, which can then be converted by familiar sequences to the diisocyanate, the diamine and the diisothio-cyanate, all of which will be useful for chain construction.

Diacids 44 and 45 can each be treated with strong base to form the corresponding carbonate anion derivatives. The diamines can be similarly degraded with strong base to form the anion cage diamines, which can then be treated with phosgene or thiophosgene to form diisocyanates or diisothiocyanates.

The polyhedral borane dianion chemistry shown above offers even more attractive possibilities here for facile generation of homodifunctional chain forming reagents. Compound 29, OC—{12B—2}—CO, will be a particularly versatile intermediate, as will its —{1-0B—2}— counterpart, whose synthesis is shown below.

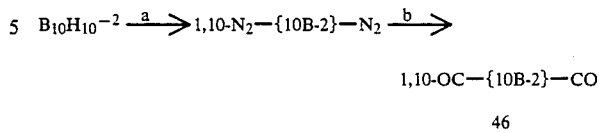

1,10-OC—{10B-2}—CO    46

(a) HONO
(b) CO, heat
Knoth et al., J. Am. Chem. Soc., 89, 4842(1967) Muetterties et al., "Polyhedral Boranes", op. cit.

The borane dicarbonyls are remarkably easy to transform into other useful molecules, as seen below, wherein B-CO denotes one end of the borane dicarbonyl function, both ends behaving similarly.

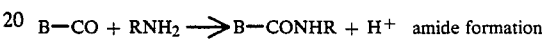    amide formation

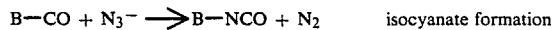    isocyanate formation

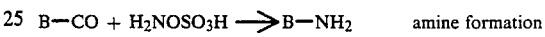    amine formation

It has been noted earlier that attempts to form amino acids with metallocarboranes often produce "by-products" having diacid or diamine groups, as shown in the synthesis of compound 43. Where the homodifunctional compound is the desired product, it can be produced in high yield by analogy to the earlier procedures. Thus, compounds 47 and 48 are readily produced from treating Solution A, alone, or Solution B, alone, with cobaltous chloride, with air workup.

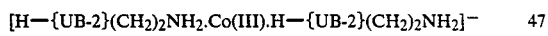    47

    48

Compound 44 can be converted to its carborane dianion by successively stronger base treatments, and combined with unsubstituted dicarbollide and CoCl₂, with air workup, to produce diacid 49.

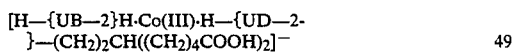    49

It will be recalled that diacids such as 48 and 49 can readily be converted to diisocyanates, diamines and diisothiocyanates.

Prior to cleavage of the PAUT from the polymer resin support, it is useful to cap the N-terminus of the chain with a linker group which, after cleavage of the chain, will serve to link the polymer to the antibody. The linker will preferably have at least one function capable of reacting with a (deblocked) amine and another function which is sufficiently stable to cleavage conditions to survive, while being reactive with pendant groups on the antibody molecule for formation of a covalent bond. The antibody-linking function can be present as such on the linker or as a precursor of masked function.

One advantageous function for antibody linkage is the isothiocyanate group, the isocyanate and the activated acid being useful as well. Amine-reactive groups include benzyl halides, acid halides, anhydrides, OSu esters, and the like. Typical capping groups include, e.g., p-isothiocyanatobenzyl bromide, p-isothiocyanatobenzoyl bromide, p-isothiocyanatophenacyl bromide, and the like.

Alternatively, the N-terminal amine can be deblocked and capped with a group that renders it unreactive, after which the C-terminal carboxyl is cleaved and activated so that it functions as the antibody-linking group. One approach would be to cap the N-terminal amine 8deblocked) with an cetyl group, then cleave the C-terminal carboxyl, and convert the acid to an OSu ester by reaction with HOSu/DCC. This ester could bind to the antibody, or it could be reacted with excess diamine, and the resultant amine converted to an isothiocyanate with thiophosgene. Other permutations will occur to the ordinary skilled artisan.

Without further elaboration, it is believed that one skilled in the art can, using the preceding description, utilize the present invention to its fullest extent. The following preferred specific embodiments are, therefore, tobe construed as merely illustrative, and not limitative of the remainder of the disclosure in any way whatsoever. In the following examples, all temperatures are set forth uncorrected in degrees Celsius; unless otherwise indicated, all parts and percentages are by weight.

The polymers prepared in the following examples are made using a Beckman Model 990 Automated Peptide Synthesizer, and purified using a Beckman Model 340 HPLC system. The basic reagents and procedures are taken from Stewart et al., "Solid Phase Peptide Synthesis, 2nd. Ed.", except where noted. Boron-containing compounds are prepared using 96% B-10-enriched $B_{10}H_{14}$ (Callery Chemical Co., Callery, Pa.), and reagents derived therefrom by conventional reactions shown herein. Resin beads, BOC-protected natural amino acids and beta-alanine, and standard reagents are all available commercially and can be prepared by conventional means, should commercial sources no longer be available.

The following abbreviations are used in the examples:

| Symbol | Meaning |
| --- | --- |
| [P] | Merrifield resin of polystyrene crosslinked with 1% divinylbenzene (DVB) |
| [P]—O—gly-BOC | Above resin (hydroxymethylated) containing 0.4 meq/g esterified BOC—glycine (Peninsula Labs., Inc., Belmont, CA.) |
| [P]—O—Bal-BOC | Above resin (hydroxymethylated) containing 0.4 meq/g esterified BOC—beta-alanine (Peninsula) |
| TFA | trifluoroacetic acid |
| TEA | triethylamine |
| DCC | dicyclohexylcarbodiimide |
| DCM | dichloromethane (solvent) |
| CA-T | Chloramine-T |
| AddRes | Standard sequence for addition of an amino acid residue (see below) |
| Weld | Sequence for joining shorter oligomers to form longor oligomer (see below) |
| Ab | Antibody or antibody fragment |
| S-Y | Stewart et al., op. cit |

EXAMPLE 1

Synthesis of a Boron-Loaded Polypeptide (a) Synthesis of reagents.

Compounds 1, 2, 5, and 11–14 are separately reacted with BOC-Cl under standard conditions (see, e.g., S-Y, pp. 61-4) to produce the N-BOC derivative of each. Each BOC-amino acid (1-BOC, 2-BOC, etc.) is supplied to the appropriate reservoir of the synthesizer as a 0.10M solution in DCM. DCC is supplied as a 1M solution in DCM. TFA is supplied as a 1:3 v:v TFA:DCM mixture with 1 mg/ml indole added. TEA is supplied as a 1:9 v:v reagent grade TFA:DCM solution. Resin is supplied as 2.0 g (0.8 meq) [P]—O—gly—BOC.

(b) Synthesis of Building Block (BB) decapeptide.

The starting resin is charged to the reaction flask of the peptide synthesizer, and subjected to an AddRes sequence with 2-BOC (in step 8A) as follows:

| Step | Reagent | Vol (ml) | Time (min) |
| --- | --- | --- | --- |
| 1 | DCM wash (×3) | 30 | 1.5 |
| 2 | TFA/DCM/indole | 30 | 1.5 |
| 3 | TFA/DCM/indole | 30 | 30 |
| 4 | DCM wash (×6) | 30 | 1.5 |
| 5 | TEA/DCM | 30 | 1.5 |
| 6 | TEA/DCM | 30 | 1.5 |
| 7 | DCM wash (×6) | 30 | 1.5 |
| 8A | BOC-aa/DCM | 20 | 1.5 |
| 9B | DCC/DCM | 2 | 120* |
| 9 | DCM wash (×3) | 30 | 1.5 |

*Each coupling reaction is monitored after about 120 min. reaction, by withdrawal of a small portion of resin, which is subjected to the Kaiser ninhydrin qualitative color test. A blue color signifies incomplete coupling, and requires repeating steps 4-8, with a 160 min. coupling time.

The resultant [P]—O—gly—2—BOC is subjected to successive AddRes sequence with 12-BOC, 1-BOC, 13-BOC, 5-BOC, 11-BOC, 14-BOC, 2-BOC, 12-BOC and 13-BOC, respectively to produce the BOC-BB peptide, [P]-O-gly-2-12-1-13-5-11-14-2-12-13-BOC, as its glycyl-resin conjugate.

After successful completion of the synthetic sequence, the resin conjugate is deblocked (steps 1–7 of the AddRes sequence), and the resin is transferred to an HF cleavage apparatus, e.g., HF Reaction Apparatus Type I (Peninsula). The cleavage reaction is conducted with 4 ml of anisole per 0.8 meq of resin. Cleavage with liquid HF (40 ml) is carried out at 0° C. for 45 min. and then pumped down to dryness under vacuum. The resin is immediately transfered to a fritted glass funnel using 20 ml of dry ethyl acetate (EtOAc), washed with 3×20 ml of EtOAc, and the washings discarded. The resin is then extracted with 4×60 ml of 1M aqueous acetic acid (HOAc), followed by 3.·30 ml glacial HOAc. The extracts are combined, treated with 0.5 ml of TEA, and immediately lyophilized. The solid residue is the resultant BB peptide, HO-gly-2-12-1-13-5-11-14-2-12-13-NH2, as the triethylammonium salts of the anionic residues 5, 12 and 14. Final purification is achieved by HPLC, typically using an Altech/Beckman Ultrasphere ODS column, operated with a 240 nm uv detector, eluted with 50:50 v:v $CH_3CN:H_2O$, with 0.1M HOAc/-TEA buffer, pH 4.5. The purified BB peptide is recovered by lophilization of peptide-rich eluate, which also removes the volatile buffer, and stored at −30° C. Yields are about 80% of purified peptide (m.w., 3588 daltons), as the tetrakis(triethylammonium) salt.

(c) Synthesis of 50-residue peptide.

The reaction flask of the peptide synthesizer is charged with 0.5 g (0.2 meq) of [P]—O—Bal—BOC. The BB peptide is prepared as a 0.027M solution in DCM, such that 15 ml of the solution contains 1.44 g (0.4 mmol) of the peptide. Diacid 45 is converted to the corresponding diamine, 45a, by conventional Schmidt degradation, and thence to the corresponding bis-isocyanate, 45b, with phosgene. These are supplied to the peptide synthesizer as 0.1M solutions in DCM, and TEA and TFA/indole are supplied as in part (a) hereof. The Weld sequence is effected on the esterified resin as follows:

| Step | Reagent | Vol (ml) | Time (min) |
|---|---|---|---|
| 1 | DCM wash (×3) | 15 | 1.5 |
| 2 | TFA/DCM/indole | 15 | 1.5 |
| 3 | TFA/DCM/indole | 15 | 30 |
| 4 | DCM wash (×6) | 15 | 1.5 |
| 5 | TEA/DCM | 15 | 1.5 |
| 6 | TEA/DCM | 15 | 1.5 |
| 7 | DCM wash (×6) | 15 | 1.5 |
| 8 | 45b/DCM | 15 | 120 |
| 9 | DCM wash (×6) | 15 | 1.5 |
| 10 | BB peptide/DCM | 15 | 180 |
| 11 | DCM wash (×6) | 15 | 1.5 |
| 12 | DCC/DCM | 1.5 | 1.5 |
| 13 | 45a/DCM | 15 | 180 |
| 14 | DCM wash (×6) | 15 | 1.5 |

The foregoing Weld sequence results in attachment of a bis-isocyanate linker to the resin, to which the glycyl-BB peptide is then bound through another urethane linkage. The free carboxyl terminus of the BB peptide is then condensed with one amine of a diamine linker, preparatory to iteration of steps 8–14 of the Weld sequence with another portion of BB peptide solution to attach another glycyl-decapeptide to the resin-bound chain. Three more iterations of steps 8–14 of the Weld sequence are performed to grow a urethane-bridge 50-residue chain on the resin, incorporating 5 BB peptide segments.

The resultant Large Peptide is capped with a selective sequentional bifunctional linker, e.g., bis(p-isothiocyanato)benzoic anhydride (IBA). The latter compound is prepared by reacting p-isothiocyanatobenzoic acid (Fairfield Chemical Co., Blythewood, S.C.) with an excess of thionyl chloride in benzene, azeotropically removing water, e.g., with a Dean-Stark trap, cooling the resultant solution, and collecting the crystalline IBA. The end capping is effected by adding 15 ml of a 0.1M solution of IBA anhydride to the resin-bound Large Peptide, and allowing the reaction to proceed for 120 min. The resin is then washed with 6×15 ml DCM, and the capped Large Peptide is cleaved from the resin under the HF cleavage conditions of part (b) hereof, using proportionally smaller amounts of reagents. The combined HOAC extracts from the cleavage step are lyphilized, and the resultant capped peptide is further purified by HPLC.

The product contains 580 boron atoms per molecule, has a molecular weight of about 22,000 Daltons, and is represented by the condensed structure

HOOCCH$_2$CH$_2$NH(CONH45bNHCONH—B-B—CONH45aNH)$_5$COPhNCS.

It will be appreciated that many other combinations of amino acids disclosed herein can be prepared by minor and conventional modifications of the foregoing procedures, to produce a broad array of polymers falling within the generic scope of the invention. The peptide chains can be grown by addition of individual residues, short oligopeptide sequences, or longer oligopeptides, optionally linked with Weld sequence-type residues. The type of polymer illustrated by this Example, containing mostly polypeptide chains, optionally linked by a minor proportion of urethane or thiocarbamate junctions, represents a subclass of polymeric conjugate formers according to the invention generally referred to as "predominantly polypeptide".

EXAMPLE 2

Production of Boron-Loaded Antibody Conjugate

A sample of NP-2 murine monoclonal anti-CEA IgG (U.S. Ser. No. 609,607) is reacted with a threefold molar excess of capped Large Peptide, prepared according to Example 1(c) hereof, in a buffered aqueous solution, at pH 6 (phosphate buffer). The pH is raised to 7.5 by cautious addition of NaOH, preferably using a pH meter and/or pH-Stat. The reaction is allowed to proceed overnight, at 0° C. The resultant conjugate is freed of unreacted Large Peptide by brief passage through a sizing column, e.g., PD-10 Sephadex G-25, pre-equilibrated with 1% normal human serum albumin in phosphate-buffered saline (PBS), and eluted with the same medium.

The recovered conjugate is stored as a sterile solution containing, per ml:
(1) 10 mg Human Serum Albumin (HSA) (1%, USP, Parke-Davis)
(2) 0.01M phosphate buffer, pH7.5 (Bioware)
(3) 0.9% NaCl
(4) 100 ug conjugate

EXAMPLE 3

Production of Radioiodinated Boron/Antibody Conjugate

The capped Large Peptide prepared according to Example 1(c) hereof is radioiodinated by reaction with CA-T, at 0° C., using carrier-free Na$^{131}$I (Amersham-Searle), by the procedure of Example 1(f) of U.S. Pat. No.4,348,376, except that the amount of capped Large peptide per mCi of $^{131}$I is adjusted so that iodination results in introduction of about 1–10 iodine atoms per Large Peptide. Iodination occurs substantially only on the carborange anions, of which there are 20 per Large Peptide. The product can be freed of iodination by-products by washing on a 10K-pass Millipore filter, using 0.01M phosphate buffer at pH 6. The final concentration of iodinated Large Peptide should be about 1 mg/ml.

The iodinated Large Peptide is conjugated to antibody according to the procedure of Example 2, and the conjugate, having an average of one Large Peptide per antibody and a specific activity of about 100 uCi/ug, is purified and stored analogously.

It will be appreciated that radioiodination can also be effected with $^{125}$I, for production of antibody conjugates for in vitro or in vivo (i.e., normally animal) studies, or with $^{123}$I, for radioimmunodetection or other uses. Similarly, it will be appreciated that the many other antibodies and antibody fragments which specifically bind markers produced by or associated with tumors or pathological lesions, disclosed in the above-referenced patents and patent applications, as well as those known to the art and those yet to be discovered, can all be conjugated to predominantly polypeptide polymers according to the invention.

The resultant conjugates include conjugates containing large numbers of boron atoms and/or, in the case where other diagnostically or therapeutically useful addends are bound to side chains of the polypeptide, conjugates containing chelates of radiometal ions or of paramagnetic metal ions (optionally high loadings, e.g., of paramagnetic ions for magnetic resonance image enhancement, or of radioisotopes for therapy), conjugates containing drugs or toxins, conjugates containing markers useful for in vitro assays (e.g., fluorescent groups, enzymes, chromophores and/or chromogens, and the like), conjugates containing photosensitizers, and the like.

EXAMPLE 4

Production of Boron-Loaded Antibody Conjugate

The BB peptide prepared according to Example 1 hereof, as its tetrakis(triethylammonium) salt, is dissolved in 50% by volume aqueous methanol and passed through a short column of sodium-loaded Dowex 50 cation exchange resin, to produce the sodium salt. The methanol is taken off under aspirator pressure, 0.02M phosphate buffer is added, to adjust the pH to 8.5, with cautious addition of NaOH if necessary, and the resultant solution, containing about 1 mg/ml of peptide, is treated with a tenfold molar excess of IBA, as a 1M solution in benzene, in the presence of 0.1 g $Et_4NI$ as a phase transfer agent. The mixture is vigorously agitated at room temperature for 1 hr., and the benzene layer is then separated and discarded. The aqueous layer is filtered through a 1K-pass Millipore filter to remove small soluble impurities, and the residue is redissolved at 1 mg/ml, in 0.01M phosphate buffer, pH 6.5, at 0° C.

The resultant isothiocyanate-capped BB peptide is radioiodinated with Na $^{123}$I, according to the procedure of Example 3 hereof, except that the capped Large Peptide is replace by capped BB peptide. Conditions are adjusted so that 1-4 iodine atoms per BB peptide are introduced (substantially only on carborane anions). The resultant labeled peptide, optionally further purified by Millipore filtration or column gel chromatography, is reacted with anti-CEA monoclonal antibody according to the procedure of Example 3 hereof, except that a tenfold excess of labeled capped BB peptide is used, and the resultant conjugate contains an average of about 5 peptide addends per antibody.

The conjugate is produced in a yield of about 70–80%, with an immunoreactivity of at least about 85% of that of the initial antibody. It is purified and stored analogously to the conjugates of Examples 2 and 3.

EXAMPLE 5

Synthesis of "Nylon-66-type" polyamide

A 21-residue polyamide, with alternating orientations of the amide linkage, produced by condensation of homofunctional diamines and dicarboxylates or diacylium components, is constructed using the automated peptide synthesizer and a solid phase resin support, but with a simplified condensation sequence which obviates the need for protecting groups/deprotection steps in the chain building process. The polyamide is chosen so that it has short hydrophilic (anionic) and short hydrophobic (carborane) segments interspersed with one another.

The constituent residues are: diacid 45; related diamine 45a; the carborane anion corresponding to 45a produced by treatment thereof with base, viz., $H_2N(CH_2)_3$—{UB—}—$(CH_2)_3NH_2$, denoted 45c; and diacylium compound 46. They are supplied to the reaction system as 0.1M solutions in DCM. DCC is supplied as a 1M solution in DCM. TFA is supplied as a 1:3 v:v TFA:DCM mixture with 1 mg/ml indole added. TEA is supplied as a 1:9 v:v reagent grade TFA-DCM solution, except when used to liberate a free amine group in a coupling step, in which case it is supplied as a 1M solution in DCM and denoted 1M TEA.

A 2 g quantity of esterified Merrified resin, [P]—O—gly—BOC, as in Example 1 hereof, is charged to the reaction vessel of a peptide synthesizer. The following sequence of steps is effected to produce the polyamide:

| Step | Reagent | Vol (ml) | Time (min) |
|---|---|---|---|
| 1 | DCM wash (×3) | 30 | 1.5 |
| 2 | TFA/DCM/indole | 30 | 1.5 |
| 3 | TFA/DCM/indole | 30 | 30 |
| 4 | DCM wash (×6) | 30 | 1.5 |
| 5 | TEA/DCM | 30 | 1.5 |
| 6 | TEA/DCM | 30 | 1.5 |
| 7 | DCM wash (×6) | 30 | 1.5 |
| 8A | 45/DCM | 20 | 1.5 |
| 8B | DCC/DCM | 2 | 120 |
| 9 | DCM wash (×3) | 30 | 1.5 |
| 10A | 45c/DCM | 20 | 1.5 |
| 10B | DCC/DCM | 2 | 120 |
| 11 | DCM wash (×3) | 30 | 1.5 |
| 12 | TEA/DCM | 30 | 1.5 |
| 13 | DCM wash (×3) | 30 | 1.5 |
| 14A | 45/DCM | 20 | 1.5 |
| 14B | DCC/DCM | 2 | 120 |
| 15 | DCM wash (×3) | 30 | 1.5 |
| 16A | 45c/DCM | 20 | 1.5 |
| 16B | DCC/DCM | 20 | 120 |
| 17 | DCM wash (×3) | 30 | 1.5 |
| 18A | 46/DCM | 20 | 1.5 |
| 18B | 1M TEA | 8 | 120 |
| 19 | DC wash (×3) | 30 | 1.5 |
| 20A | 45a/DCM | 20 | 1.5 |
| 20B | 1M TEA | .8 | 1.5 |
| 20C | DCC/DCM | 2 | 120 |
| 21 | DCM wash (×3) | 30 | 1.5 |

Repeat steps 14A, 14B and 15 (add 45).
Repeat steps 20A, 20B, 20C and 21 (add 45a).
Repeat steps 18A, 18B and 19 (add 46).
Repeat steps 10A through 19 (add 45c-45-45c-46).
Repeat steps 20A, 20B, 20C and 21 (add 45a).
Repeat steps 14A, 14B and 15 (add 45).
Repeat steps 20A, 20B, 20C and 21 (add 45a).
Repeat steps 18A, 18B and 19 (add 46).
Repeat steps 10A, 10B and 11 (add 45c).
Repeat steps 14A, 14B and 15 (add 45).
Repeat steps 20A, 20B, 20C and 21 (add 45a).

Upon completion of the polyamide assembly sequence, the cations associated with the anionic residues are converted to lithium ions by treatment of the resin-bound polymer with 100 ml of 0.1M $LiOOCCF_3$ in DCM, the treatment being repeated twice more, followed by 3×30 ml DCM washes for 1.5 min each. Next, the resin beads are dried in a stream of dry nitrogen, and suspended in 30 ml of dry, peroxide-free tetrahydrofuran (THF). After swelling of the beads is complete, 4 mmol (106 mg) of $LiBH_4$ are added in small portions to the stirred resin suspension, and stirring is continued at 25° C. for about 1 hr. The polyamide is thereby cleaved from the resin under mild conditions, as the terminal alcohol (reduction of the ester-resin linkage to $CH_2OH$). This precaution is taken to avoid cleavage of the somewhat labile amide linkages to residue 46, which can revert to acylium groups if subjected to strong acid conditions such as the HF or TFA used to cleave protecting groups or ester-resin bonds.

Addition of 1 ml of glacial HOAc destroys excess borohydride, and the resin is then extracted with 6×15 ml portions of glacial HOAc. The combined extracts and the THF filtrate are lyophilized. The recovered Li+ polyamide is dissolved in 50 ml (0.1M) phosphate buffer, pH 8, and shaken vigorously at 0° C. with a tenfold molar excess of IBA, supplied as a 1M solution in benzene, in the presence of 0.1 g of $Et_4NI$ as a phase transsfer agent. After 1 hr, the aqueous capped polyamide phase is separated and concentrated to 20 ml by Micropore filtration. A 50 ml portion of 0.1M phosphate buffer, pH 7.5, is added, and the solution is again concentrated to 20 ml, whereby the cations associated with the anionic residues are exchanged for Na+ ions.

EXAMPLE 6

Production of Antibody Conjugates (a) The capped polyamide produced according to Example 5 hereof is conjugated to a F(ab')$_2$ fragment from affinity purified goat anti-CEA (produced according to Example 1 of U.S. Pat. No. 4,331,647). The conjugation reaction is effected using the procedure of Example 2 hereof, with a fivefold molar excess of capped polyamide over antibody fragment. The resultant conjugate has an average of 2.5 polyamide addends per antibody fragment. Purified conjugate can be stored as a lyophilizate or in steile solution, analogously to Example 2.

(b) The capped polyamide can be radioiodinated prior to conjugation, using the procedure of Example 3 hereof, to introduce up to 5 $^{131}$I atoms per polyamide chain, thus, up to about 12.5 $^{131}$I atoms per fragment molecule after conjugation under conditions which introduce about 2.5 iodopolyamides per antibody fragment.

It will be appreciated that other antibodies and other fragments can be used instead of those illustrated herein, e.g., antibodies to AFP, HCG or its beta-subunit, CSAp, PAP, other tumor-associated markers and pathological lesion-associated markers. Other diacid/diacylium and diamine residues can be used in the polyamide assembly sequence, taken from the other representative classes and types disclosed hereinabove, and obvious variants thereof. It is also possible to use residues which need not contain boron, and which carry other addends of diagnostic or therapeutic interest, as noted hereinabove.

EXAMPLE 7

Synthesis of Branched Poly(amide/urea/thiourea)

A hybrid polymer is prepared, having amide, urea and thiourea linkages, and illustrating a chain branching option using selectively protected lysine. The resultant polymer also contains metallocarborane residues and easily iodinated residues. Two terminal amino protecting groups are used, BOC and Bpoc, having widely different acid lability. The Bpoc group can be cleaved in 0.2% TFA/DCM, the BOC group being about 120,000 times less reactive under those conditions. The BOC group requires concentrated TFA/DCM for cleavage. The synthesis proceeds by construction of a linear portion containing epsilon-BOC-protected lysine residues, onto which is built a polyurea segment having a temporarily capped terminal amine residue. Next, the lysine protecting groups are cleaved, and polyurea branches are grown and capped with a thiourea. Finally, the temporary amine cap is removed and the polymer is cleaved from the resin. A linker is used to cap the free polymer, after which it is optionally iodinated and conjugated to antibody.

Residues used for this sequence include: amino acids 11, 12 and 14, each in the form of its Bpoc derivative prepared by conventional procedures, and supplied as 0.1M solutions in DCM; alpha-Bpoc-epsilon-BOC-L-lysine $Et_4N$ salt (Chemical Dynamics Corp., South Plainfield, N.J.), also as a 0.1M solution in DCM; diamine 45c, as its inner salt (zwitterion of protonated amine and carborane anion), as a 0.1M solution in DCM; zwitterionic diamine 45c-ClZ (o-chlorobenzyloxycarbonyl protecting group on the unprotected amine of 45c (prepared from 45c and o-chlorobenzyl chloroformate, by standard S-Y procedures), as a 0.1M solution in DCM; metallocarborane diamine 47, as its neutral inner salt, as a 0.1M solution in DCM; diisocyanate 45b, as a 0.1M solution in DCM; isocyanate 46, as a 0.2M solution in DCM; and isothiocyanate 16, as a 0.2M solution in DCM. The Bpoc-protected reagents are stored at dry ice/ethanol bath temperature and allowed to warm to room temperature only when introduced into the synthesizer reaction vessel. TEA and TFA are supplied as in Example 1(a) hereof, the latter solution being denoted herein as TFA (conc.). A TFA (dil.) solution is also used, which contains 0.2% by volume TFA in DCM, with the same amount of added indole.

A 2 g (0.8 meq) sample of esterified Merrifield resin, [P]-O-gly-BOC, as in Example 1 hereof, is charged to the reaction vessel of a peptide synthesizer. The following sequence of steps is effected to produce the branched poly(amide/urea):

| Step | Reagent | Vol (ml) | Time (min) |
| --- | --- | --- | --- |
| 1 | DCM wash (×3) | 30 | 1.5 |
| 2 | TFA (conc.) | 30 | 1.5 |
| 3 | TFA (conc.) | 30 | 30 |
| 4 | DCM wash (×6) | 30 | 1.5 |
| 5 | TEA/DCM | 30 | 1.5 |
| 6 | TEA/DCM | 30 | 1.5 |
| 7 | DCM wash (×6) | 30 | 1.5 |
| 8A | Bpoc-aa/DCM (11 Bpoc) | 20 | 1.5 |
| 8B | DCC/DCM | 2 | 120* |
| 9 | DCM wash (×6) | 30 | 1.5 |
| 10 | TFA (dil.) | 30 | 1.5 |
| 11 | TFA (dil.) | 30 | 30 |
| 12 | DCM wash (×6) | 30 | 1.5 |
| 13 | TEA/DCM | 30 | 1.5 |
| 14 | TEA/DCM | 30 | 1.5 |
| 15 | DCM wash (×6) | 30 | 1.5 |
| 16 | Repeat steps 8A through 15 ten more times, using as Bpoc-aa in step 8A, respectively, 12-Bpoc, BOC—lys—Bpoc, 11-Bpoc, 12-Bpoc, BOC—lys—Bpoc, 11-Bpoc, 12-Bpoc, BOC—lys—Bpoc, 11-Bpoc, 14-Bpoc. | | |
| 17 | 45b/DCM | 20 | 120 |
| 18 | DCM wash (×6) | 30 | 1.5 |
| 19A | 45c/DCM | 20 | 120 |
| 19B | TEA/DCM | 8 | 120 |
| 20 | DCM wash (×6) | 30 | 1.5 |
| 21 | 45b/DCM | 20 | 120 |
| 22 | DCM wash (×6) | 30 | 1.5 |
| 23A | 45c-ClZ/DCM | 20 | 1.5 |
| 23B | TEA/DCM | 8 | 120 |
| 24 | DCM wash (×6) | 30 | 1.5 |
| 25 | TFA(conc.) | 30 | 1.5 |
| 26 | TFA(conc.) | 30 | 30 |
| 27 | DCM wash (×6) | 30 | 1.5 |
| 28 | TEA/DCM | 30 | 1.5 |

-continued

| Step | Reagent | Vol (ml) | Time (min) |
|---|---|---|---|
| 29 | TEA/DCM | 30 | 1.5 |
| 30 | DCM wash (×6) | 30 | 1.5 |
| 31 | 45b/DCM | 60 | 120 |
| 32 | DCM wash (×6) | 30 | 1.5 |
| 33A | 45c/DCM | 60 | 120 |
| 33B | TEA/DCM | 24 | 120 |
| 34 | DCM wash (×6) | 30 | 1.5 |
| 35 | 45b/DCM | 60 | 120 |
| 36 | DCM wash (×6) | 30 | 1.5 |
| 37A | 47/DCM | 60 | 1.5 |
| 37B | TEA/DCM | 24 | 120 |
| 38 | DCM wash (×6) | 30 | 1.5 |
| 39 | 16/DCM | 50 | 120 |
| 40 | DCM wash (×6) | 30 | 1.5 |

*Each coupling reaction is monitored after about 120 min. reaction, by withdrawal of a small portion of resin, which is subjected to the Kaiser ninhydrin qualitative color test. A blue color signifies incomplete coupling, and requires repeating steps 4-8, with a 160 min. coupling time.

Following step 40, the resin is dried under a stream of dry nitrogen, transferred to the liquid HF reactor, and cleaved with 40 ml of liquid HF containing 4 ml of anisole, at 0° C. for 45 min. This removes the ClZ protecting group from the terminal amine on the main chain and cleaves the resin-polymer ester bond, liberating the C-terminal carboxylate. The resin is then worked up and the poly(amide/urea) recovered and purified as in Example 1(b) hereof. The HLPC-purified polymer, as its $Et_3NH$ salt, is lyophilized and stored at −30° C.

It will be of interest to note that the chromophore in residues derived from 47 permits determination of concentration by visible spectroscopy, while the phenylthiourea group derived from capping with 16 permits uv monitoring.

The resultant polymer has the schematic structure:

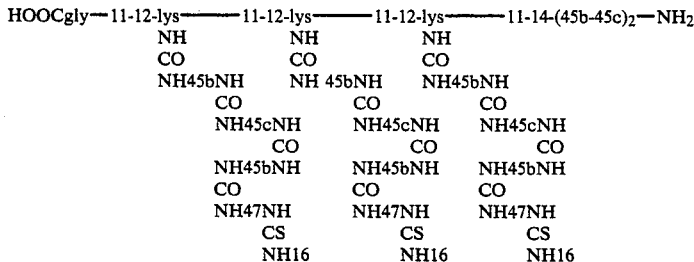

The polymer is capped with IBA by the procedure of Example 5 hereof, at close to 0° C., and optionally iodinated on the carborane anion residues by the procedure of Example 3 hereof.

EXAMPLE 8

Production of Antibody Conjugates

The capped polymer produced in Example 7 hereof is conjugated to whole IgG or F(ab')₂ fragments which specifically bind tumor or lesion markers, according to the procedures of Examples 2, 3, or 6 hereof. Alternatively, conjugation to a hybrid fragment having one arm which binds AFP and one which binds HCG (prepared according to Example 2(b) of U.S. Pat. No. 4,331,647) is effected by the procedure of Example 6 hereof, except that the hybrid fragment is used instead of the anti-CEA F(ab')₂. The iodinated conjugates are stored analogously to Example 3 hereof.

EXAMPLE 9

Synthesis of a Chelate-Loaded Polythiourea

A polythiourea is prepared, using chain branching groups as a means of functional group amplification. In this example, the highly branched chains are capped with diethylenetriaminepentaacetate (DTPA) chelators. Several readily iodinated carborane anion-containing residues are also included, which can facilitate dual tracer studies comparing the relative stabilities of radioiodine and radiometal in antibody conjugates. The nature of the chelator-loaded polythiourea is such that the metal ion can be incorporated prior to conjugation of the polymer with antibody, thereby avoiding many problems of current radiolabeling methods.

The synthesis uses as the chain splitter 3,5-diaminobenzoic acid, with both amino groups converted to their BOC-beta-alanyl amide derivatives. This species is made by conventional reaction of the 3,5-diaminobenzoic acid starting material with an excess of BOC-beta-alanine N-hydroxysuccinimide ester, which in turn is prepared from BOC-beta-alanine U.S. Biochemical Corp., Cleveland, OH.) and N-hydroxysuccinimide, with DCC/DMF at 0° C. The chain splitter is denoted CS(BOC)₂. A variant of this structure is made as a point for attaching a final capping function. This is the mixed diamine of 3,5-diaminobenzoic acid with BOC-beta-alanine and ClZ-beta-alanine, denoted CS(BOC)(ClZ), and prepared by reacting 3,5-diaminobenzoic acid with a mixture of BOC-beta-alanine N-hydroxysuccinimide ester and ClZ-beta-alanine N-hydroxysuccinimide ester [made from ClZ-beta-alanine (U.S. Biochem). and HOSu, as above]. These are supplied to the reaction as 0.1M solutions in DCM.

Diisothiocyanate 45d is prepared from diamine 45a, as described hereinabove, and provided as a 0.1M solution in DCM. Diamine 45c is provided as an inner salt, as a 0.1M solution in DCM. Diamine 45a is provided as its TFA salt, as a 0.1M solution in DCM. TEA, TFA and DCC are supplied as in Example 1(a) hereof.

A 2 g (0.8 meq) sample of esterified Merrifield resin, [P]-O-gly-BOC, as in Example 1 hereof, is charged to the reaction vessel of a peptide synthesizer. The following sequence of steps is effected to produce the branched polythiourea:

| Step | Reagent | Vol (ml) | Time (min) |
|---|---|---|---|
| 1 | DCM wash (×3) | 30 | 1.5 |
| 2 | TFA (conc.) | 30 | 1.5 |
| 3 | TFA (conc.) | 30 | 30 |
| 4 | DC wash (×6) | 30 | 1.5 |
| 5 | TEA/DCM | 30 | 1.5 |
| 6 | TEA/DCM | 30 | 1.5 |
| 7 | DCM wash (×6) | 30 | 1.5 |
| 8A | CS(BOC)(ClZ) | 20 | 1.5 |

| Step | Reagent | Vol (ml) | Time (min) |
|---|---|---|---|
| 8B | DCC/DCM | 2 | 120 |
| 9 | DCM wash (×6) | 30 | 1.5 |
| 10 | TFA (conc.) | 30 | 1.5 |
| 11 | TFA (conc.) 30 | 30 | |
| 12 | DCM wash (×6) | 30 | 1.5 |
| 13 | TEA/DCM | 30 | 1.5 |
| 14 | TEA/DCM | 30 | 1.5 |
| 15 | DCM wash (×6) | 30 | 1.5 |
| 16 | 45d/DCM | 20 | 120 |
| 17 | DCM wash (×6) | 30 | 1.5 |
| 18A | 45c/DCM | 20 | 1.5 |
| 18B | 1M TEA/DCM | 8 | 120 |
| 19 | DCM wash (×6) | 30 | 1.5 |
| 20 | 45d/DCM | 20 | 120 |
| 21 | DCM wash (×6) | 30 | 1.5 |
| 22A | 45a/DCM | 20 | 1.5 |
| 22B | 1M TEA/DCM | 8 | 120 |
| 23 | DCM wash (×6) | 30 | 1.5 |
| 24A | CS(BOC)$_2$ | 20 | 1.5 |
| 24B | DCC/DCM | 2 | 120 |
| 25 | DCM wash (×6) | 30 | 1.5 |
| 26-31 | Repeat steps 2-7 | | |
| 32-47 | Repeat steps 16-31, using doubled amounts of reagents | | |
| 48-63 | Repeat steps 16-31, using quadrupled amounts of reagents | | |
| 64-79 | Repeat steps 1-31, using octupled amounts of reagents | | |

After completion of step 79, eight polythiourea chains have been elaborated in a tree-like configuration stemming from one of the two amine functions on the initial chain splitter, viz., the one with the BOC-beta-alanyl amide. The remaining amine is preserved as the ClZ-beta-alanyl amide, which survives the conditions used up to this point. The eight terminal amine functions are now capped with (HOOCCH$_2$)$_2$NCH(CH$_2$C$_6$H$_4$NCS)CH$_2$N-(COOH)CH$_2$CH$_2$N(CH$_2$COOH)$_2$, as the dry sodium salt, 12 mmol/50 ml dry dimethylformamide (DMF), used in excess, at room temperature. The isothiocyanatobenzyl-DTPA (DTPA-NCS) is described by Chang et al., "Applications of Nuclear and Radiochemistry", Lambrecht et al, Ed., Chap. 10 (Pergamon Press, New York, NY, 1982). The resin is freed of DCM and swelled with DMF prior to reaction with the DTPA-NCS. Following the capping reaction, the resin is washed with 6×30 ml of DMF, and then washed, swollen and washed again with 6×30 ml of DCM. The resin is then dried under a stream of dry nitrogen and treated with 100 ml of liquid HF containing 10 ml of anisole, at 0° C., for 1 hr. This removes the ClZ protecting group from the second amine on the chain splitter and cleaves the resin-polymer ester bond, liberating the C-terminal carboxylate. The resin is then worked up and the polythiourea is recovered and purified as in Example 1(b) hereof. The HLPC-purified polymer, as its Et$_3$NH salt, is lyophilized and stored at −30° C.

The polymer is capped with IBA by the procedure of Example 5 hereof, at close to 0° C., and optionally iodinated on the carborane anion residues by the procedure of Example 3 hereof. The capped polythiourea, either radioiodinated or not, is incubated with an excess of either a radiometal, e.g., $^{67}$GaCl$_3$, $^{111}$InCl$_3$, $^{90}$YCl$_3$, SnCl$_2$-reduced $^{99m}$TcO$_4$−, or the like, under standard conditions, to chelate the radiometals, or with paramagnetic ions, e.g., solutions of GdCl$_3$, EuCl$_3$, or the like.

EXAMPLE 10

Production of Chelate-Loaded Antibody Conjugates

The capped polymer produced in Example 9 hereof, either iodinated or not, and carrying a radiometal or a paramagnetic ion, is conjugated to whole IgG or F(ab')$_2$ fragments which specifically bind tumor or lesion markers, according to the procedures of Examples 2, 3, or 6 hereof. Alternatively, conjugation to a hybrid fragment having one arm which binds AFP and one which binds HCG (prepared according to Example 2(b) of U.S. Pat. No. 4,331,647) is effected by the procedure of Example 6 hereof, except that the hybrid fragment is used instead of the anti-CEA F(ab')$_2$. The conjugates are stored analogously to Example 3 hereof.

EXAMPLE 11

Production of Highly Chelate-Loaded Polymer

Amplification of the chelate loading achieved in Examples 9 and 10 hereof can readily be achieved using the same components, but combining the steps. Thus, the capped polythiourea produced in Example 9 hereof can be substituted for the Meares DTPN-NCS after the last iteration of the branching sequence, to load each of the eight terminal amines with eight chelates, rather than just one, resulting in 64 chelate groups on the resin-bound polymer prior to cleavage and final capping with IBA. Several of these 64-chelate addends can be conjugated to antibody, after loading with radiometal ions or paramagnetic ions, either with or without iodination of the reactive carborane anion groups. It will be appreciated that further iterations of the sequence and/or further branching of the chains can be effected to increase the amplification. More highly branched chain splitters can also be used, as disclosed hereinabove, to achieve this result.

Antibody fragments, especially Fab and Fab' fragments, can be linked to bivalent polymers carrying chelates, through thioether linkages to a pair of haloamide caps, or through, e.g., urea or thiourea linkages to a pair of isocyanate or isothiocyanate caps. Bivalent polymers are easily prepared, e.g., by using a BOC/ClZ-lysine residue, terminating the chain with an amine, cleaving with HF, and reacting the liberated epsilon-NH$_2$ and the terminal amine with IBA. Many other variants will be apparent to the skilled artisan, in light of the copious disclosure hereinabove.

EXAMPLE 12

Neutron Activated Tumor Radiotherapy

The procedure of Example 7 of U.S. Pat. No. 4,348,376 is used to effect therapy by injection of a patient with a radioiodinated, boron-loaded anti-CEA antibody, scanning with a gamma camera to locate the site or sites of uptake of the labeled antibody, and then directing a beam of thermal neutrons at the tumor site. The present example differs from that in the referenced patent by substitution of the conjugate prepared according to Example 3 hereof for the conjugate used in the reference. This offers the advantage that a much higher boron loading is achieved, both because of the use herein of 96% Boron-10 starting materials, and because 580 boron atoms per antibody are carried to the tumor site. Injection of 0.9 mg of conjugate, preferably as three injections of 300 ng each, spaced 3-6 hrs apart, will carry about 1.22 ug of Boron-10 to a 1 g tumor, even if only 4% of the injected antibody is localized in the tumor. This is within the therapeutic range of 1-30 ug $^{10}$B/g tumor which is considered adequate for this therapy.

It will be appreciated that the boron-loaded conjugates disclosed in the other Examples herein can also be used for analogous therapeutic treatments such as those disclosed in the other herein referenced Goldenberg patents and patent applications. Highly radiolabeled conjugates can also be used for therapy, according to the teachings of the referenced patents and patent applications, or according to art-recognized methods of others in this field.

EXAMPLE 13

Radioimmunodetection of Tumors and Lesions

Tumor localization is effected according to the procedure of Example 7 of U.S. Pat. No. 4,361,544, except that the labeled antibody is the radioiodinated conjugate of Example 6(b) hereof, the antibody being an anti-HCG affinity-purified goat IgG or a monoclonal anti-HCG IgG. Imaging results are comparable. Alternatively, $^{67}$Ga-labeled antibody prepared according to the procedures of Examples 9 and 10 hereof, using anti-CEA IgG, and $^{111}$In-labeled irrelevant IgG can be used in place of the specific and irrelevant IgGs of Example 10 of U.S. Pat. No. 4,444,744 to achieve imaging of colorectal tumors with high resolution.

Example 2 of U.S. Ser. No. 633,999, U.S. Pat. No. 4,624,846, can be effected using the conjugate according to Example 3 herein, except that the antibody is the same murine monoclonal anti-HSV-1 F(ab')$_2$ in the reference example. Results are comparable.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A modified antibody or antibody fragment, consisting essentially of:
   (1) at least one hypervariable region which specifically binds a ligand such that the formation of the resultant immunological complex is of diagnostic or therapeutic utility; and
   (2) at least one defined, substantially homogeneous synthetic sequenced polymer whose constituent residues are linked by amide or urea or thiourea linkages or a combination thereof, and which incorporates residues containing a plurality of Boron-10 atoms;
   wherein said synthetic sequenced polymer is chemically bound to said antibody or antibody fragment at one or more sites which do not substantially interfere with the immunological specificity of said hypervariable region.

2. The modified antibody or antibody fragment of claim 1, wherein said synthetic sequenced polymer is a polyamide.

3. The modified antibody or antibody fragment of claim 2, wherein said polyamide has a "Nylon 66" structure along substantially all of its backbone.

4. The modified antibody or antibody fragment of claim 1, wherein said synthetic sequenced polymer is a polythiourea.

5. The modified antibody or antibody fragment of claim 1, wherein said ligand is a marker which is produced by or associated with a tumor or a pathological lesion.

6. The modified antibody or antibody fragment of claim 3, containing 50-2000 boron atoms per antibody/fragment.

7. The modified antibody or antibody fragment of claim 6, containing 200-2000 boron atoms per antibody or antibody fragment.

8. The modified antibody or antibody fragment of claim 7, wherein said boron atoms are about 96% enriched with Boron-10 isotope.

9. The modified antibody or antibody fragment of claim 2, wherein said polyamide is formed of condensed amino acids a major portion of which contain boron cage structures.

10. The modified antibody or antibody fragment of claim 9, wherein said condensed amino acids are natural amino acids or their enantiomers having pendant amine, hydroxyl, carboxyl or thio groups to which are bound at least one carborane-containing group.

11. The modified antibody or antibody fragment of claim 9, wherein said condensed amino acids are selected from those having the formulas

| | |
|---|---|
| H—{DB}—C$_6$H$_4$NHC(S)NH(CH$_2$)$_4$CH(NH$_2$)COOH | 1 |
| H—{DB}—(CH$_2$)$_3$C(O)NH(CH$_2$)$_4$CH(NH$_2$)COOH | 2 |
| H—{DB}—C$_6$H$_4$NHC(S)OCH$_2$CH(NH$_2$)COOH | 3 |
| H—{DB}—C$_6$H$_4$NHC(O)(CH$_2$CH(NH$_2$)COOH | 4 |
| M$^+$ H—{UB—}—C$_6$H$_4$NHC(S)NH(CH$_2$)$_4$CH(NH$_2$)COOH | 5 |
| M$^+$ H—{UB—}—C$_6$H$_4$NHC(S)NH(CH$_2$)$_4$CH(NH$_2$)COOH | 6 |
| M$^+$ H—{UB—}—(CH$_2$)$_4$C(O)NH(CH$_2$)$_4$CH(NH$_2$)COOH | 7 |
| H—{DB}—C$_6$H$_4$N=N—(OH)C$_6$H$_3$CH$_2$CH(NH$_2$)COOH | 8 |
| H—{DB}—(CH$_2$)$_3$S(CH$_2$)$_2$CH(NH$_2$)COOH | 9 |
| H—{DB}—(CH$_2$)$_3$OC$_6$H$_4$CH$_2$CH(NH$_2$)COOH | 10 |
| H—{DB}—(CH$_2$)$_3$CH(NH$_2$)COOH | 11 |
| M$^+$ H—{UB—}—(CH$_2$)$_4$CH(NH$_2$)COOH | 12 |
| H$_2$N(CH$_2$)$_3$—{DB}—(CH$_2$)$_3$COOH | 13 |
| M$^+$ H$_2$N(CH$_2$)$_3$—{UB—}—(CH$_2$)$_3$COOH | 14 | wherein {DB} is a dicarba-closo-dodecaborane group; {UB—} is a dicarba-nido-undecaborane anionic group; and {IUB—} is an iodo-dicarba-nido-undecaborane anionic group having one vertex of the {UB—} group replaced by a BI in the cage structure; and M$^+$ represents one equivalent of an alkali metal, an alkali earth metal or a quaternary ammonium cation.

12. In a method of tumor or pathological lesion radiotherapy, which comprises injecting a human subject parenterally with an antibody or antibody fragment which specifically binds a marker produced by or associated with said tumor or lesion and which is conjugated to an addend comprising a plurality of atoms of Boron-10 isotope, permitting said antibody or antibody fragment to accrete in said tumor or lesion or its immediate vicinity by binding to said marker, and directing a beam of thermal neutrons at said patient,
   the improvement wherein said boron-labeled antibody or antibody fragment is a modified antibody/fragment according to claim 1.

13. A kit for use in neutron-activated radiotherapy of a tumor or pathological lesion, comprising a sterile preparation of a boron-labeled modified antibody or antibody fragment according to claim 1, suitable for preparing an injectable composition for parenteral injection in a human subject.

14. The modified antibody or antibody fragment of claim 2, wherein said ligand is a marker which is produced by or associated with a tumor or a pathological lesion.

15. The modified antibody or antibody fragment of claim 1, containing 50–2000 boron atoms per antibody or antibody fragment.

16. In a method of tumor or pathological lesion radiotherapy, which comprises injecting a human subject parenterally with an antibody or antibody fragment which specifically binds a marker produced by or associated with said tumor or lesion and which is conjugated to an addend comprising a plurality of atoms of Boron-10 isotope, permitting said antibody or antibody fragment to accrete in said tumor or lesion or its immediate vicinity by binding to said marker, and directing a beam of thermal neutrons at said patient, the improvement wherein said boron-labeled antibody or antibody fragment is a modified antibody or antibody fragment according to claim 2.

17. A kit for use in neutron-activated radiotherapy of a tumor or pathological lesion, comprising a sterile preparation of a boron-labeled modified antibody or antibody fragment according to claim 2, in a suitable container, suitable for preparing an injectable composition for parenteral injection in a human subject.

* * * * *